United States Patent
Richardson et al.

(10) Patent No.: US 11,311,552 B2
(45) Date of Patent: Apr. 26, 2022

(54) THERAPIES FOR CANCER

(71) Applicant: PROXIMAGEN, LLC, Plymouth, MN (US)

(72) Inventors: Peter Richardson, Haverhill Suffolk (GB); Jacqueline Mary Walling, Hillsborough, CA (US); Claudio Festuccia, L'Aquila (IT)

(73) Assignee: Proximagen, LLC, Plymouth, MN (US)

( * ) Notice: Subject to any disclaimer, the term of this patent is extended or adjusted under 35 U.S.C. 154(b) by 0 days.

(21) Appl. No.: 15/562,741

(22) PCT Filed: Apr. 1, 2016

(86) PCT No.: PCT/IB2016/051880
§ 371 (c)(1),
(2) Date: Sep. 28, 2017

(87) PCT Pub. No.: WO2016/157149
PCT Pub. Date: Oct. 6, 2016

(65) Prior Publication Data
US 2018/0078563 A1     Mar. 22, 2018

Related U.S. Application Data

(60) Provisional application No. 62/141,980, filed on Apr. 2, 2015.

(51) Int. Cl.
*A61K 31/551* (2006.01)
*A61K 9/00* (2006.01)
*A61K 45/06* (2006.01)

(52) U.S. Cl.
CPC .......... *A61K 31/551* (2013.01); *A61K 9/0019* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,939,098 A * | 8/1999 | Reidenberg | A61K 31/55 424/451 |
| 6,191,130 B1 | 2/2001 | Patoiseau et al. | |
| 9,353,086 B2 | 5/2016 | Savory et al. | |
| 10,155,761 B2 | 12/2018 | Savory et al. | |
| 2006/0235028 A1 | 10/2006 | Li et al. | |
| 2013/0210811 A1 | 8/2013 | Ryu et al. | |
| 2013/0216531 A1 | 8/2013 | Jain et al. | |
| 2013/0266630 A1 * | 10/2013 | Khaw | A61K 9/0051 424/422 |
| 2013/0289020 A1 | 10/2013 | Savory et al. | |
| 2016/0046606 A1 | 2/2016 | Savory et al. | |
| 2017/0226106 A1 | 8/2017 | Savory et al. | |
| 2018/0078563 A1 | 3/2018 | Richardson et al. | |

FOREIGN PATENT DOCUMENTS

| | | |
|---|---|---|
| CN | 100339080 | 10/2005 |
| EP | 0 431 580 A2 | 6/1991 |
| EP | 1 571 146 A1 | 9/2005 |
| EP | 1 849 781 A1 | 10/2007 |
| WO | 94/15928 A1 | 7/1994 |
| WO | 98/25617 A1 | 6/1998 |
| WO | 00/02870 | 1/2000 |
| WO | 01/14333 A1 | 3/2001 |
| WO | 02/02539 A1 | 1/2002 |
| WO | 03/020716 A1 | 3/2003 |
| WO | 03/082855 A1 | 10/2003 |
| WO | 2004/089913 A1 | 10/2004 |
| WO | 2004/099176 A1 | 11/2004 |
| WO | 2005/059107 A2 | 6/2005 |
| WO | 2006/071875 A1 | 7/2006 |
| WO | 2006/071958 A1 | 7/2006 |
| WO | 2006/088836 A2 | 8/2006 |
| WO | 2006/088840 A1 | 8/2006 |
| WO | 2006/088919 A2 | 8/2006 |
| WO | 2006/088920 A1 | 8/2006 |
| WO | 2006/088921 A2 | 8/2006 |
| WO | 2006/130426 A2 | 12/2006 |
| WO | 2006/138259 A2 | 12/2006 |
| WO | 2007/071952 A1 | 6/2007 |
| WO | 2007/109238 A1 | 9/2007 |
| WO | 2008/008453 A1 | 1/2008 |
| WO | 2008/028553 A1 | 3/2008 |
| WO | 2008/036379 A2 | 3/2008 |
| WO | 2008/060621 A2 | 5/2008 |
| WO | 2008/079279 A1 | 7/2008 |
| WO | 2008/094992 A2 | 8/2008 |

(Continued)

OTHER PUBLICATIONS

Rubin et al. "A Small Molecule Antagonist of CXCR4 Inhibits Intracranial Growth of Primary Brain Tumors". PNAS. 2003; 100(23):13513-13518. (Year: 2003).*
Ehtesham et al. "CXCR4 Expression Mediates Glioma Cell Invasiveness". Oncogene. 2006; 25:2801-2806. (Year: 2006).*
Zheng et al. "CXCR4-Positive Subset of Glioma Is Enriched for Cancer Stem Cells". Oncol Res. 2011; 19(12):555-561. [Abstract Only] (Year: 2011).*
Kioi et al. "Inhibition of Vasculogenesis, But Not Angiogenesis, Prevents the Recurrence of Glioblastoma After Irradiation in Mice". J Clin Invest. 2010; 120(3):694-705. (Year: 2010).*
International Search Report issued in PCT/EP2011/067946, dated Jan. 31, 2012.

(Continued)

*Primary Examiner* — Leslie A. Royds Draper
(74) *Attorney, Agent, or Firm* — Ballard Spahr LLP

(57) ABSTRACT

The invention relates to 6-{4-[1-(Propan-2-yl)piperidin-4-yl]-1,4-diazepan-1-yl}-N-(pyridin-4-yl)pyridine-2-carboxamide, or a pharmaceutically acceptable salt thereof, for use in treatment of CNS cancers. The invention also relates to combination treatments with irradiation and/or a chemotherapeutic agent for use in the treatment of cancer.

7 Claims, 12 Drawing Sheets

(56) References Cited

FOREIGN PATENT DOCUMENTS

| WO | 2008/121065 A1 | 10/2008 | |
|---|---|---|---|
| WO | 2009/071701 A1 | 6/2009 | |
| WO | 2010/054006 A1 | 5/2010 | |
| WO | 2011/008915 A1 | 1/2011 | |
| WO | 2012/049277 A1 | 4/2012 | |
| WO | WO-2014094178 A1 * | 6/2014 | ........... C07D 241/20 |
| WO | WO 2017/153780 | 9/2017 | |
| WO | WO 2018/162924 | 9/2018 | |

OTHER PUBLICATIONS

International Search Report issued in PCT/IB2016/051880, dated May 23, 2016.
European Search Report issued in EP Patent Application No. 15158267.3, dated Jul. 1, 2015.
Berardi et al., "Novel 4-(4-Aryl)cyclohexyl-1-(2-pyridyl)piperzines as $\Delta_8$-$\Delta_7$ Sterol Isomerase (Emopamil Binding Protein) Selective Ligands with Antiproliferative Activity", *J. Med. Chem.*, vol. 51, pp. 7523-7531, 2008.
Averin et al., "Amination of 2-Chloro- and 2,4-Dichloropyrimidines by Polyamines", *Chemistry of Heterocyclic Compounds*, vol. 44, No. 9, pp. 1146-1157, 2008.
Haas, "Two Edges of Sickle Cell Disease," *SciBX*, vol. 4, No. 3, pp. 1-16, 2011.
Strekowski et al., "Amplification of Bleomycin-Mediated Degradation of DNA by Polyamines" *Anti-Cancer Drug Design*, vol. 3, pp. 79-89, 1988.
Broxmeyer et al., "Rapid Mobilization of Murine and Human Hematopoietic Stem and Progenitor Cells with AMD3100, a CXCR4 Antagonist", *JEM*, vol. 201, No. 8, pp. 1307-1318, 2005.
Chen et al., "Understanding and Targeting Cancer Stem Cells: Therapeutic Implications and Challenges", *Acta Pharmacologica Sinica*, vol. 34, pp. 732-740, 2013.
Colmone et al., "Leukemic Cells Create Bone Marrow Niches That Disrupt the Behavior of Normal Hematopoietic Progenitor Cells", *Science*, vol. 322, pp. 1861-1865, 2008.
Croker et al., "Cancer Stem Cells: Implications for the Progression and Treatment of Metastatic Disease", *J. Cell. Mol. Med.*, vol. 12, No. 2, pp. 374-390, 2008.
Bensinger et al., "Improving Stem Cell Mobilization Strategies: Future Directions", *Bone Marrow Transplantation*, vol. 43, pp. 181-195, 2009.
Hermann et al., "Distinct Populations of Cancer Stem Cells Determine Tumor Growth and Metastatic Activity in Human Pancreatic Cancer", *Cell Stem Cell*, vol. 1, pp. 313-323, 2007.
Kioi et al., "Inhibition of Vasculogenesis, But Not Angiogenesis, Prevents the Recurrence of Glioblastoma after Irradiation in Mice", *J. Clin. Invest.*, vol. 120, No. 3, pp. 694-705, 2010.
Kopp et al., "The Bone Marrow Vascular Niche: Home of HSC Differentiation and Mobilization", *Physiology*, vol. 20, pp. 349-356, 2005.
Micallef et al., "Successful Stem Cell Remobilization Using Plerixafor (Mozobil) Plus Granulocyte Colony-Stimulating Factor in Patients with Non-Hodgkin Lymphoma: Results from the Plerixafor NHL Phase 3 Study Rescue Protocol", *Biol. Blood Marrow Transplant*, vol. 15, pp. 1578-1586, 2009.
Pitchford et al., "Differential Mobilization of Subsets of Progenitor Cells from the Bone Marrow", *Cell Stem Cell* vol. 4, pp. 62-72, 2009.
Redjal et al., "CXCR4 Inhibition Synergizes with Cytotoxic Chemotherapy in Gliomas", *Clin. Cancer Res.*, vol. 12, pp. 6765-6771, 2006.
Zagzag et al. "Hypoxia- and Vascular Endothelial Growth Factor-Induced Stromal Cell-Derived Factor-1/CXCR4 Expression in Glioblastomas: One Plausible Explanation of Scherer's Structures", *AJP*, vol. 173, No. 2, 2008.
Zlotnik, "New Insights on the Role of CXCR4 in Cancer Metastasis", *J. Pathol.*, vol. 215, pp. 211-213, 2008.
Wang et al., "The Pivotal Role of CXCL12 (SDF-1)/CXCR4 Axis in Bone Metastasis", *Cancer Metastasis Rev.*, vol. 25, pp. 573-587, 2006.
Yang et al., "Morphology and Quantitative Composition of Hematopoietic Cells in Murine Bone Marrow and Spleen of Healthy Subjects", *Ann. Hematol.*, vol. 92, pp. 587-594, 2013.
Bing, X. et al., "Study on the expression levels of CXCR4, CXCL12, CD44, and CD147 and their potential correlation with invasive behaviors of pituitary adenomas," Biomed Environ Sci, 2013; 26(7): 592-598.
Zhi, Y. et al., "NF-κB signaling pathway confers neuroblastoma cells migration and invasion ability via the regulation of CXCR4," Med Sci Monit, 2014; 20: 2746-2752.
Razmkhah, M. et al., "Expression of chemokines and chemokine receptors in brain tumor tissue derived cells," Asian Pac J Cancer Prev, 2014; 15(17): 7201-7205.
Klein, S. et al., "CXCR4 promotes neuroblastoma growth and therapeutic resistance through miR-15a/16-1-mediated ERK and BCL2/cyclin D1 pathways," Cancer Res. Mar. 15, 2018;78(6): 1471-1483.
Gong, J. et al., "High expression levels of CXCL12 and CXCR4 predict recurrence of adamanti-nomatous craniopharyngiomas in children," Cancer Biomarkers 14 (2014) 241-251.
Bianchi, F. et al., "Central nervous system (CNS) neuroblasoma. A case-based update," Child's Nervous System (2018) 34:817-823.
D Tseng, DA Vasquez-Medrano and JM Brown, "Targeting SDF-I/CXCR4 to inhibit tumour vasculature for treatment of glioblastomas", British Journal Cancer (2011), 104(12), 1805-1809.
Examination Report Action dated Jun. 18, 2020 by the Australian Patent Office for AU Application No. 2016242118, filed Apr. 1, 2016, and published as AU 2016242118 on Oct. 6, 2016 (Applicant—Proximagen, LLC) (4 Pages).
Gelmini, et al. (2008) "The critical role of SDF-1/CXCR4 axis in cancer and cancer stem cells metastasis" J Endocrinol Invest 31(9): 809-19.
Zhang and Xu (2017) "A new insight in chimeric antigen receptor-engineered T cells for cancer immunotherapy," J Hematol Oncol 10(1): 1.
Examination Report dated Oct. 13, 2020 by the European Patent Office for EP Application No. 18711658.7, filed Mar. 9, 2018, and published as EP 3592356 on Jan. 15, 2020 (Applicant—Proximagen, LLC) (7 Pages).
Final Office Action dated Mar. 24, 2020 by the U.S. Patent and Trademark Office for U.S. Appl. No. 16/167,084, filed Oct. 22, 2018 (Applicant—Proximagen, LLC) (37 Pages).
Response to Office Action filed on Aug. 13, 2020, with the U.S. Patent and Trademark Office for U.S. Appl. No. 16/167,084, filed Oct. 22, 2018 and published as US 2019-0062333 A1 on Feb. 28, 2019 (Applicant—Proximagen, LLC) (37 pages).
Non-Final Office Action dated Sep. 8, 2020 by the U.S. Patent and Trademark Office for U.S. Appl. No. 16/167,084, filed Oct. 22, 2018 (Applicant—Proximagen, LLC) (5 Pages).
Final Office Action dated Nov. 30, 2020 by the USPTO Patent Office for U.S. Appl. No. 16/167,084, filed Oct. 22, 2018, and published as US 2019-0062333 on Feb. 28, 2019 (Applicant—Proximagen, LLC) (7 Pages).
Dunussi-Joannopoulos et al. (2002) "Efficacious immunomodulatory activity of the chemokine stromal cell-derived factor 1 (SDF-1): local secretion of SDF-1 at the tumor site serves as T-cell chemoattractant and mediates T-cell-dependent antitumor responses" *Blood* 100(5): 1551-1558.
Feig, et al. (2013) "Targeting CXCL12 from FAP-expressing carcinoma-associated fibroblasts synergizes with anti-PD-L1 immunotherapy in pancreatic cancer" *PNAS* 110(50): 20212-20217.
Fushimi, et al. (2006) "Adenoviral gene transfer of stromal cell-derived factor-1 to murine tumors induces the accumulation of dendritic cells and suppresses tumor growth" *Cancer Res* 66(7): 3513-3522.
Gravina et al. (2017) "New development in CAR-T cell therapy" *J Hematol Oncol* 10(1): 1-16.
Joyce, et al. (2015) "T cell exclusion, immune privilege, and the tumor microenvironment" *Science* 348(6230): 74-80.

(56) References Cited

OTHER PUBLICATIONS

Kozin, et al. (2010) "Recruitment of myeloid but not endothelial precursor cells facilitates tumor regrowth after local irradiation" *Cancer Res* 70(14): 5679-5685.

Kumar, et al. (2006) "CXCR4 physically associates with the T cell receptor to signal in T cells" *Immunity* 25: 213-224.

Mukherjee, et al. (2013) "The Role of chemokine receptor CXCR4 in breast cancer metastasis" *Am J Cancer Res* 3(1): 46-57.

Nomura, et al. (2001) "Enhancement of anti-tumor immunity by tumor cells transfected with the secondary lymphoid tissue chemokine EBI-1-ligand chemokine and stromal cell-derived factor-1alpha chemokine genes" *Int J Cancer* 91: 597-606.

Richardson (2016) "CXCR4 and Glioblastoma" *Anticancer Agents Med Chem* 16: 59-74.

Righi, et al. (2011) "CXCL12/CXCR4 blockade induces multimodal antitumor effects that prolong survival in an immunocompetent mouse model of ovarian cancer" *Cancer Res* 71(16): 5522-5534.

Rubin, et al. (2003) "A small-molecule antagonist of CXCR4 inhibits intracranial growth of primary brain tumors" *PNAS* 100(23): 13513-13518.

Vianello, et al. (2006) "Murine B16 melanomas expressing high levels of the chemokine stromal-derived factor-1/CXCL12 induce tumor-specific T cell chemorepulsion and escape from immune control" *J Immunol* 176: 2902-2914.

Wermuth, et al. (2002) Handbook of Pharmaceutical Salts: Properties, Selection and Use (Wiley-VCH, Weinheim, Gerrmany), pp. 1-7.

Williams, et al. (2010) "Multiple functions of CXCL12 in a syngeneic model of breast cancer" *Mol. Cancer* 9: 250.

Zheng, et al. (2001) "CXCR4-positive subset of glioma is enriched for cancer stem cells" *Oncol Res* 19(12): 555-561.

Gosalbez et al. (2014) "Differential expression of stroma derived factor-1 isoforms in bladder cancer," *J Urol* 191(6): 1899-1905.

Retz et al. (2005) "CXCR4 expression reflects tumor progression and regulates motility of bladder cancer cells," *Int J Cancer* 114: 182-189.

\* cited by examiner

— TEMOZOLOMIDE ALONE (A);

⋯⋯⋯ 6-{4-[1-(PROPAN-2-yl)PIPERIDIN-4-yl]-1, 4-DIAZEPAN-1-yl}-N-(PYRIDIN-4-yl)PYRIDINE-2-CARBOXAMIDE ALONE (B);

------ COMBINATION OF 6-{4-[1-(PROPAN-2-yl)PIPERIDIN-4-yl]-1, 4-DIAZEPAN-1-yl}-N-(PYRIDIN-4-yl)PYRIDINE-2-CARBOXAMIDE AND TEMOZOLOMIDE (C)

—— RADIOTHERAPY ALONE (A);

·········· 6-{4-[1-(PROPAN-2-yl)PIPERIDIN-4-yl]-1, 4-DIAZEPAN-1-yl}-N-(PYRIDIN-4-yl)PYRIDINE-2-CARBOXAMIDE ALONE (B);

------ COMBINATION OF 6-{4-[1-(PROPAN-2-yl)PIPERIDIN-4-yl]-1, 4-DIAZEPAN-1-yl}-N-(PYRIDIN-4-yl)PYRIDINE-2-CARBOXAMIDE AND RADIOTHERAPY (C)

——— VEHICLE (A);

············ SUNITINIB ALONE (B);

— — — — 6-{4-[1-(PROPAN-2-yl)PIPERIDIN-4-yl]-1, 4-DIAZEPAN-1-yl}-N-(PYRIDIN-4-yl)
PYRIDINE-2-CARBOXAMIDE ALONE (C);

— ·· — ·· — COMBINATION OF 6-{4-[1-(PROPAN-2-yl)PIPERIDIN-4-yl]-1, 4-DIAZEPAN-1-yl}-N-
(PYRIDIN-4-yl)PYRIDINE-2-CARBOXAMIDE AND SUNITINIB (D)

THERAPIES FOR CANCER

CROSS-REFERENCE TO RELATED APPLICATIONS

This Application is a national phase application under 35 U.S.C. § 371 of International Application No. PCT/IB2016/051880, filed on Apr. 1, 2016, which claims the benefit of U.S. Provisional Application No. 62/141,980, filed on Apr. 2, 2015, the contents of which are hereby incorporated by reference in their entireties.

INTRODUCTION

The invention described herein relates to the use of CXCR4 antagonist 6-{4-[1-(Propan-2-yl)piperidin-4-yl]-1,4-diazepan-1-yl}-N-(pyridin-4-yl)pyridine-2-carboxamide in the treatment of cancers of the CNS. The invention further relates to the use of 6-{4-[1-(Propan-2-yl)piperidin-4-yl]-1,4-diazepan-1-yl}-N-(pyridin-4-yl)pyridine-2-carboxamide in combination with irradiation and/or a chemotherapeutic agent for the treatment of cancer, including cancers of the CNS.

BACKGROUND TO THE INVENTION

CXCR4 is a G-protein coupled receptor whose natural endogenous ligand is the cytokine SDF-1 (stromal derived factor-1; also referred to as CXCL12). CXCR4 was first discovered as a co-receptor, with CD4, for the entry of T-cell line-tropic (X4) HIV-1 into T-cells. CXCR4 manipulation (in combination with granulocyte colony stimulating factor (G-CSF)) has proven to improve the outcome of haematopoietic (Broxmeyer et al., 2005) and endothelial progenitor cell (Pitchford et al., 2009) stem cell mobilization. The CXCR4-SDF-1 interaction is also a master regulator of cancer stem cell trafficking in the human body (Croker and Allan, 2008) and plays a key role in the progression and metastasis of various types of cancer cells in organs that highly express SDF-1 (Zlotnik, 2008).

Several types of cancers (including non-small cell lung, breast and glioblastoma) express CXCR4 and SDF-1 which are strongly implicated in the maintenance of cancer stem cells (Wang et al., 2006; Croker and Allan, 2008) and in the recurrence of tumours after therapy. In addition CXCR4 has been shown to have a role in the formation of new blood vessels in experimental tumours (Kioi et al., 2010).

Of particular interest is the observation that CXCR4 expression in many cancers is associated with a small population of cells which exhibit stem cell-like characteristics i.e. they are tumourigenic. These stem cell-like cells are enriched under specific tissue culture conditions (serum free plus EGF and FGF) and are heavily implicated in mediating metastatic spread (see e.g. Hermann et al., 2007). In cancers of the CNS (including primary brain tumours) these cells are strongly implicated in the spread of the cancer through the brain (Zagzag et al., 2008).

In humans, cancers of the CNS include gliomas, the most common type of primary brain tumours. Gliomas originate from the supporting glial cells of the brain, and are typically associated with grave prognosis. Based on the originating cell, gliomas include: astrocytomas, ependymomas, oligodendrocytomas, glioblastomas, oligodendrogliomas, and others. High-grade astrocytomas, which include glioblastoma multiformans (GBM) and anaplastic astrocytoma (AA), are the most common intrinsic brain tumours in adults.

Gliomas are histologically defined by whether they exhibit primarily astrocytic or oligodendroglial morphology. Gliomas are graded by cellularity, nuclear atypia, necrosis, mitotic figures, and micro-vascular proliferation—all features associated with biologically aggressive behaviour. This system of diagnosis has been developed over decades of clinical experience with gliomas and has now become the cornerstone of neuro-oncology. The World Health Organization classification scheme of astrocytic gliomas is divided into four (4) grades. Less malignant tumours fall under Grade I (pilocytic astrocytoma) and Grade II (astrocytic glioma), whereas the more malignant tumours are designated Grade III (anaplastic astrocytoma) and Grade IV (GBM). Oligodendrogliomas and mixed gliomas (gliomas with both oligodendroglial and astrocytic components) occur in low-grade (Grade II) and more malignant variants (Grade III).

These tumours are typically treated on first diagnosis with a combination of surgery, focused irradiation and the DNA alkylating agent temozolomide. However, in some patients, the tumours re-grow suggesting that the tumours are, or have become, resistant to temozolomide. Resistance to temozolomide is frequently a consequence of the expression of the DNA repair enzyme O-6-methylguanine-DNA methyltransferase (MGMT). Metastatic cancers of the CNS (i.e. those which arise as a result of spread from peripheral cancers such as breast and lung) are treated in a similar fashion, although whole brain rather than focused irradiation is sometimes used. Treatment of CNS cancers by surgery is not always possible or desirable, for example the tumour may be inaccessible (e.g. deep in the brain) or the patient may be incapable of withstanding the trauma of neurosurgery, perhaps because they are elderly and/or infirm. Irradiation (radiotherapy) and treatment with a cytotoxic agent (chemotherapy) are known to have undesirable side effects. Therefore an unmet medical need exists for treatments for CNS cancers, including cancers of the brain. Few chemotherapeutic agents penetrate the brain sufficiently to reach an effective therapeutic concentration therein, which makes difficult the treatment of CNS cancers with systemically administered chemotherapeutic agents. One agent which does enter the brain is lomustine, a DNA alkylating agent which has been used widely in clinical trials of brain cancers. Others include temozolomide, carmustine, irinotecan and carboplatin.

Studies report the treatment of CNS cancers in mice using a combination of the CXCR4 antagonist AMD3100 and irradiation or a chemotherapeutic agent (e.g. Redjal et al., 2006; and Chen et al., 2013). However, it is expected that patients treated with the combination of AMD3100 and radiotherapy and/or a chemotherapeutic agent will experience greater toxic side effects than patients treated with AMD3100 or the radiotherapy and/or chemotherapeutic agent alone. It is known that bone marrow provides a protective and nourishing environment for haematopoietic stem cells (HSCs) which are required to maintain the supply of blood cells. Treatment with a CXCR4 antagonist, such as AMD3100 mobilises HSCs from the bone marrow. When administered with GCSF, sufficient HSCs are mobilised to permit HSC transplantation (i.e. the HSCs are harvested and stored prior to administration to a patient who has undergone aggressive chemotherapy). This procedure is particularly useful in the treatment of bone marrow cancers such as multiple myeloma, because it permits aggressive chemotherapy with subsequent restoration of the bone marrow (Di Persio et al., 2009; Micallef et al., 2009). The cytoprotective nature of the bone marrow is seen with HSCs (Kopp et al., 2005) and some cancer stem cells such as those of acute lymphoblastic leukaemia (Colmone et al., 2008; Yang et al., 2013).

Patients treated with chemotherapy and/or radiotherapy typically experience side effects resulting from the destruction of bone marrow HSCs. Releasing the HSCs from the protective environment of the bone marrow is expected to make these side effects even worse, potentially causing anaemia and neutropenia. Therefore an unmet medical need exists for a combination of a CXCR4 antagonist and a chemotherapeutic agent for treatment of cancers, including cancers of the CNS, the treatment having a reduced risk of side effects.

CXCR4 antagonists are known in the literature. For example WO2012/049277 teaches the structure and preparation of CXCR4 antagonist 6-{4-[1-(Propan-2-yl)piperidin-4-yl]-1,4-diazepan-1-yl}-N-(pyridin-4-yl)pyridine-2-carboxamide, which is Example 30, and has the structure:

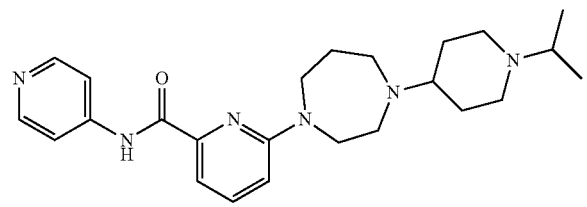 [SMILES: CC(C)N1CCC(N2CCCN(c3cccc(C(=O)Nc4ccncc4)n3)CC2)CC1]

SUMMARY OF THE INVENTION

In a first aspect of the invention, the applicant has found that 6-{4-[1-(Propan-2-yl)piperidin-4-yl]-1,4-diazepan-1-yl}-N-(pyridin-4-yl)pyridine-2-carboxamide is surprisingly effective in the treatment of CNS cancers, including cancers of the brain, also known as orthotopic (intracranial) tumours.

In a second aspect of the invention, the applicant has found that a combination of CXCR4 antagonist 6-{4-[1-(Propan-2-yl)piperidin-4-yl]-1,4-diazepan-1-yl}-N-(pyridin-4-yl)pyridine-2-carboxamide and irradiation and/or a chemotherapeutic agent is surprisingly effective (i.e. synergistic) in the treatment of cancers, including CNS cancers.

Related to the second aspect of the invention, the applicant has additionally found that treatment with a combination of 6-{4-[1-(Propan-2-yl)piperidin-4-yl]-1,4-diazepan-1-yl}-N-(pyridin-4-yl)pyridine-2-carboxamide and irradiation and/or a chemotherapeutic agent has a surprisingly reduced risk of side effects in patients. In other words, the present invention makes available a combination treatment for cancer comprising 6-{4-[1-(Propan-2-yl)piperidin-4-yl]-1,4-diazepan-1-yl}-N-(pyridin-4-yl)pyridine-2-carboxamide and irradiation and/or a chemotherapeutic agent having surprisingly improved safety.

DETAILED DESCRIPTION OF THE INVENTION

Figure 1:
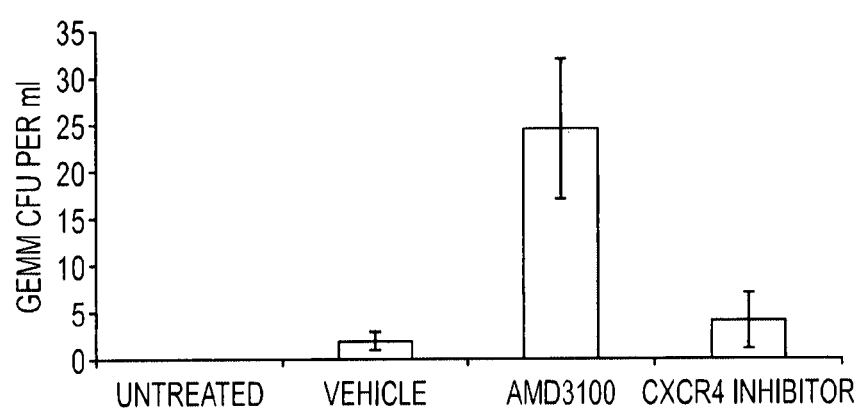
FIG. 1 is a graph showing the degree of mobilisation of haematopoietic stem cells (HSCs) and progenitor cells (CFU-GEMM) in mice following injection of vehicle, AMD3100 (5 mg/kg) and 6-{4-[1-(Propan-2-yl)piperidin-4-yl]-1,4-diazepan-1-yl}-N-(pyridin-4-yl)pyridine-2-carboxamide (30 mg/kg).

In an embodiment according to the first aspect of the invention, the applicant makes available 6-{4-[1-(Propan-2-yl)piperidin-4-yl]-1,4-diazepan-1-yl}-N-(pyridin-4-yl)pyridine-2-carboxamide, or a pharmaceutically acceptable salt thereof, for use in treatment of CNS cancers. In an embodiment the CNS cancer is cancer of the brain. In an embodiment the CNS cancer is a glioma. In an embodiment the CNS cancer is selected from the group consisting of neuroblastoma, glioblastoma, other astrocytomas, oligodendroglial tumour, meningioma, ependymoma, oligodendroglioma, medulloblastoma, and metastases into the CNS from peripheral cancers. In an embodiment, the CNS cancer is selected from glioblastoma and astrocytoma.

In an embodiment according to the first aspect of the invention, the applicant makes available the use of 6-{4-[1-(Propan-2-yl)piperidin-4-yl]-1,4-diazepan-1-yl}-N-(pyridin-4-yl)pyridine-2-carboxamide, or a pharmaceutically acceptable salt thereof, in the manufacture of a medicament for use in the treatment of CNS cancers. In an embodiment the CNS cancer is cancer of the brain. In an embodiment the CNS cancer is a glioma. In an embodiment the CNS cancer is selected from the group consisting of neuroblastoma, glioblastoma, other astrocytomas, oligodendroglial tumour, meningioma, ependymoma, oligodendroglioma, medulloblastoma, and metastases into the CNS from peripheral cancers. In an embodiment, the CNS cancer is selected from glioblastoma and astrocytoma.

In an embodiment according to the first aspect of the invention, the applicant makes available a method of treatment of a patient suffering from CNS cancer, which method comprises administering to the patient 6-{4-[1-(Propan-2-yl)piperidin-4-yl]-1,4-diazepan-1-yl}-N-(pyridin-4-yl)pyridine-2-carboxamide, or a pharmaceutically acceptable salt thereof, in sufficient amounts to provide a therapeutic effect. In an embodiment the CNS cancer is cancer of the brain. In an embodiment the CNS cancer is a glioma. In an embodiment the CNS cancer is selected from the group consisting of neuroblastoma, glioblastoma, other astrocytomas, oligodendroglial tumour, meningioma, ependymoma, oligodendroglioma, medulloblastoma, and metastases into the CNS from peripheral cancers. In an embodiment, the CNS cancer is selected from glioblastoma and astrocytoma.

In an embodiment according to the second aspect of the invention, the applicant makes available 6-{4-[1-(Propan-2-yl)piperidin-4-yl]-1,4-diazepan-1-yl}-N-(pyridin-4-yl)pyridine-2-carboxamide in combination with irradiation for treatment of cancer.

In another embodiment according to the second aspect of the invention, the applicant makes available 6-{4-[1-(Propan-2-yl)piperidin-4-yl]-1,4-diazepan-1-yl}-N-(pyridin-4-yl)pyridine-2-carboxamide in combination with one or more chemotherapeutic agents, including brain penetrating chemotherapeutic agents, for the treatment of cancer.

In another embodiment according to the second aspect of the invention, the applicant makes available 6-{4-[1-(Propan-2-yl)piperidin-4-yl]-1,4-diazepan-1-yl}-N-(pyridin-4-yl)pyridine-2-carboxamide in combination with irradiation and one or more chemotherapeutic agents for treatment of cancer.

Without wishing to be bound by theory, it is understood that the reduced risk of side effects following administration of a combination according to the second aspect of the invention results from the surprisingly low tendency of 6-{4-[1-(Propan-2-yl)piperidin-4-yl]-1,4-diazepan-1-yl}-N-(pyridin-4-yl)pyridine-2-carboxamide to mobilise haematopoietic stem cells (HSCs) from the protective environment of the bone marrow.

This reduced mobilisation has the advantage that during treatment with a combination of 6-{4-[1-(Propan-2-yl)piperidin-4-yl]-1,4-diazepan-1-yl}-N-(pyridin-4-yl)pyridine-2-carboxamide and irradiation and/or a chemotherapeutic agent, the HSCs tend to remain in the protective environment of the bone marrow and are therefore less likely to be destroyed by the irradiation and/or chemotherapeutic agent. This results in a reduced likelihood of side effects due to destruction of HSCs and consequent reduction of blood cells such as anaemia and neutropenia.

In an embodiment of the compound, use or method according to the second aspect of the invention the cancer includes the following cancers and metastases thereof: cancers of the lung (including non-small cell and small cell), pancreas, cervix, thyroid, kidney, ovary, prostate, skin (including melanoma), cancers of the GI tract (including oesophageal, hepatic, colorectal and gastric cancers), oral squamous carcinoma, cancers of the blood including leukaemias such as B-CLL, AML, CML, ALL, lymphomas such as intraocular, Non-Hodgkins and Hodgkins lymphomas, and multiple myeloma; cancers of the nervous system including cancer of the brain, neuroblastoma, glioblastoma, other astrocytomas, oligodendroglial tumour, meningioma, ependymoma, oligodendroglioma, medulloblastoma, and metastases into the CNS from peripheral cancers.

In an embodiment of the compound, use or method according to the second aspect of the invention the cancer is a CNS cancer selected from the group consisting of neuroblastoma, glioblastoma, other astrocytomas, oligodendroglial tumour, meningioma, ependymoma, oligodendroglioma, medulloblastoma, and metastases into the CNS from peripheral cancers. In an embodiment, the CNS cancer is selected from glioblastoma and astrocytoma.

In an embodiment of the compound, use or method according to the second aspect of the invention the chemotherapeutic agent is a DNA modifying agent.

In an embodiment of the compound, use or method according to the second aspect of the invention the chemotherapeutic agent is harmful or otherwise toxic towards haematopoietic stem cells, such as temozolomide.

In an embodiment of the compound, use or method according to the second aspect of the invention 6-{4-[1-(Propan-2-yl)piperidin-4-yl]-1,4-diazepan-1-yl}-N-(pyridin-4-yl)pyridine-2-carboxamide is combined with a chemotherapeutic agent is selected from the group consisting of bevacizumab, sunitinib, temozolomide, vincristine, lomustine, procarbazine, carmustine, irinotecan, cisplatin, carboplatin, methotrexate, etoposide, bleomycin, vinblastine, actinomycin D, cyclophosphamide, and ifosfamide. In a preferred embodiment, the chemotherapeutic agent is bevacizumab. In a preferred embodiment, the chemotherapeutic agent is sunitinib. In a preferred embodiment, the chemotherapeutic agent is temozolomide. In a preferred embodiment, the chemotherapeutic agent is vincristine. In a preferred embodiment, the chemotherapeutic agent is lomustine. In a preferred embodiment, the chemotherapeutic agent is procarbazine. In a preferred embodiment, the chemotherapeutic agent is carmustine. In a preferred embodiment, the chemotherapeutic agent is irinotecan. In a preferred embodiment, the chemotherapeutic agent is cisplatin. In a preferred embodiment, the chemotherapeutic agent is carboplatin. In a preferred embodiment, the chemotherapeutic agent is methotrexate. In a preferred embodiment, the chemotherapeutic agent is etoposide. In a preferred embodiment, the chemotherapeutic agent is bleomycin. In a preferred embodiment, the chemotherapeutic agent is vinblastine. In a preferred embodiment, the chemotherapeutic agent is actinomycin D. In a preferred embodiment, the chemotherapeutic agent is cyclophosphamide. In a preferred embodiment, the chemotherapeutic agent is ifosfamide.

In an embodiment of the compound, use or method according to the second aspect of the invention, following systemic administration to a patient, the chemotherapeutic agent is capable of penetrating the brain and reaching a therapeutic concentration therein. In an embodiment of the compound, use or method according to the second aspect of the invention the brain penetrating chemotherapeutic agent is selected from any one of sunitinib, lomustine, temozolomide, carmustine, irinotecan, and carboplatin. In an embodiment the brain penetrating chemotherapeutic agent is lomustine or carmustine.

In an embodiment of the compound, use or method according to the second aspect of the invention the 6-{4-[1-(Propan-2-yl)piperidin-4-yl]-1,4-diazepan-1-yl}-N-(pyridin-4-yl)pyridine-2-carboxamide is administered before administration of the irradiation and/or chemotherapeutic agent.

In an embodiment of the compound, use or method according to the second aspect of the invention the 6-{4-[1-(Propan-2-yl)piperidin-4-yl]-1,4-diazepan-1-yl}-N-(pyridin-4-yl)pyridine-2-carboxamide is administered concurrently with administration of the irradiation and/or chemotherapeutic agent.

In an embodiment of the compound, use or method according to the second aspect of the invention the 6-{4-[1-(Propan-2-yl)piperidin-4-yl]-1,4-diazepan-1-yl}-N-(pyridin-4-yl)pyridine-2-carboxamide is administered after administration of the irradiation and/or chemotherapeutic agent.

In an embodiment of the compound, use or method according to the second aspect of the invention the cancer to be treated comprises a tumour resistant to temozolomide. In an embodiment of the compound, use or method according to the second aspect of the invention the cancer to be treated comprises a tumour resistant to irradiation. In an embodiment of the compound, use or method according to the second aspect of the invention the cancer to be treated comprises a tumour resistant to temozolomide and irradiation.

In an embodiment of the compound, use or method according to the second aspect of the invention the 6-{4-[1-(Propan-2-yl)piperidin-4-yl]-1,4-diazepan-1-yl}-N-(pyridin-4-yl)pyridine-2-carboxamide is in an intravenous formulation.

In an embodiment of the compound, use or method according to the second aspect of the invention the chemotherapeutic agent is in an intravenous formulation.

In a further embodiment 6-{4-[1-(Propan-2-yl)piperidin-4-yl]-1,4-diazepan-1-yl}-N-(pyridin-4-yl)pyridine-2-carboxamide is used in combination with a chemotherapeutic agent able to penetrate the blood brain barrier.

In an embodiment, 6-{4-[1-(Propan-2-yl)piperidin-4-yl]-1,4-diazepan-1-yl}-N-(pyridin-4-yl)pyridine-2-carboxamide is used in combination with external beam radiotherapy 60Gy in 2Gy fractions.

In an embodiment, 6-{4-[1-(Propan-2-yl)piperidin-4-yl]-1,4-diazepan-1-yl}-N-(pyridin-4-yl)pyridine-2-carboxamide is used in combination with external beam radiotherapy 60Gy in 2Gy fractions and temozolomide.

It is expected that the claimed combination will be especially effective in the treatment of cancers which have become resistant or otherwise unresponsive to treatment with temozolomide and/or irradiation.

Terminology

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

As used herein, the terms "treatment of cancer" and "treatment of a CNS cancer" is not intended to be an absolute term. In some aspects, the compositions and methods of the invention seek to reduce the size of a tumor or number of cancer cells, cause a cancer to go into remission, inhibit or prevent tumor growth in size or cell number of cancer cells. In some circumstances, treatment with a compound or combination according to the claimed invention leads to an improved prognosis. Treatment as a prophylactic measure (i.e. prophylaxix) is also included. For example, a patient at risk of the occurrence or re-occurrence of cancer may be treated as described herein.

As used herein, the term "cancer" refers to the broad class of disorders characterized by hyperproliferative cell growth, either in vitro (e.g., transformed cells) or in vivo. Conditions which can be treated or prevented by the compositions and methods of the invention include, e.g., a variety of neoplasms, including benign or malignant tumours, a variety of hyperplasias, or the like. Compounds and methods of the first and second aspects of the invention can achieve the inhibition and/or reversion of undesired hyperproliferative cell growth involved in such conditions. The term "cancer" includes any solid tumor or liquid cancers, and can be metastatic or non-metastatic. Examples of cancers and their metastases susceptible to treatment with the claimed compound or combinations include cancers of the central nervous system (CNS).

As used herein, the term "cancer of the CNS" includes cancers of the brain, such as glioma, neuroblastoma, glioblastoma, other astrocytomas, oligodendroglial tumours, meningiomas, ependymomas, and medulloblastomas. A glioma is a tumour that arises from glial cells or their precursors of the brain or spinal cord. Gliomas are histologically defined based on whether they exhibit primarily astrocytic or oligodendroglial morphology, and are graded by cellularity, nuclear atypia, necrosis, mitotic figures, and microvascular proliferation—all features associated with biologically aggressive behaviour. Astrocytomas are of two main types—high-grade and low-grade. High-grade tumours grow rapidly, are well-vascularized, and can easily spread through the brain. Low-grade astrocytomas are usually localized and grow slowly over a long period of time. High-grade tumours are much more aggressive, require very intensive therapy, and are associated with shorter survival lengths of time than low grade tumours. The majority of astrocytic tumours in children are low-grade, whereas the majority in adults are high-grade. These tumours can occur anywhere in the brain and spinal cord. Some+ of the more common low-grade astrocytomas are: Juvenile Pilocytic Astrocytoma (JPA), Fibrillary Astrocytoma Pleomorphic Xantroastrocytoma (PXA) and Desembryoplastic Neuroepithelial Tumour (DNET). The two most common high-grade astrocytomas are Anaplastic Astrocytoma (AA) and Glioblastoma Multiforme (GBM).

Additional examples of cancers and their metastases susceptible to treatment with the claimed combination include cancers of the lung (including non-small cell and small cell), pancreas, cervix, thyroid, kidney, ovary, prostate, skin (including melanoma), cancers of the GI tract (including oesophageal, hepatic, colorectal and gastric cancers), oral squamous carcinoma, cancers of the blood including leukaemias such as B-CLL, AML, CML, ALL, lymphomas such as intraocular, Non-Hodgkins and Hodgkins lymphomas, and multiple myeloma.

As used herein, the term "patient suffering from cancer" refers to an individual or subject that has been diagnosed with cancer or a cell proliferative disorder.

As used herein, the term "patient suffering from CNS cancer" refers to an individual or subject that has been diagnosed with cancer of the CNS or a cell proliferative disorder of the CNS, including cancers of the brain, and orthotopic (intracranial) tumours.

As used herein, the term "chemotherapeutic agent" is any anti-cancer drug or medicament which has activity against cancer cells. Chemotherapeutic agents include monoclonal antibodies and small molecule drugs. Some small molecule chemotherapeutic drugs are cytotoxic, that is to say they act by killing cells that divide rapidly. Examples of chemotherapeutic agents include bevacizumab, sunitinib, temozolomide, vincristine, lomustine, procarbazine, carmustine, irinotecan, cisplatin, carboplatin, methotrexate, etoposide, bleomycin, vinblastine, actinomycin D, cyclophosphamide, and ifosfamide. Chemotherapeutic drugs may be administered one drug at a time (single agent chemotherapy), or in combination (combination chemotherapy). Chemotherapeutic drugs may be administered in combination with irradiation. In an embodiment, the chemotherapeutic agent is other than 6-{4-[1-(Propan-2-yl)piperidin-4-yl]-1,4-diazepan-1-yl}-N-(pyridin-4-yl)pyridine-2-carboxamide. In an embodiment, the chemotherapeutic agent is an antibody such as bevacizumab. In an embodiment, the chemotherapeutic agent is sunitinib.

Any suitable quantity and type of irradiation and/or chemotherapeutic agent may be combined with 6-{4-[1-(Propan-2-yl)piperidin-4-yl]-1,4-diazepan-1-yl}-N-(pyridin-4-yl)pyridine-2-carboxamide for use in the present invention. Suitable regimes of irradiation and examples of chemotherapeutic agents can be found in the current guidelines: 2011 Canada, Easaw et al., Current Oncology Vol 18 No 3.

As used herein the term "brain penetrating chemotherapeutic agent" means a chemotherapeutic agent which when administered systemically is able to penetrate into the brain and reach effective therapeutic concentrations therein. Examples of brain penetrating chemotherapeutic agents include sunitinib, lomustine, temozolomide, carmustine, irinotecan, and carboplatin.

As used herein the term "therapeutic effect" means providing a therapeutic response in a subject. For example, providing a therapeutic effect includes inhibiting tumour progression or tumour growth. The skilled person understands that tumour progression in human patients can be determined by a variety of methods. For example, size of a tumour close to the skin can be measured by establishing the width and depth of the tumour with calipers, and then calculating the tumour volume. Less accessible tumours, such as lung and CNS cancers can be measured by observation of the images obtained from Magnetic Resonance Imaging (MRI) scanning. CNS tumours, such as brain tumours, can be measured by a combination of MRI scanning and by monitoring neurological performance. Growth of a brain tumour is typically associated with decreasing neurological performance. Providing a therapeutic effect also includes prolonging survival of a patient or subject beyond that expected in the absence of treatment. In an embodiment treatment of a patient or subject with a compound or combination according to the first or second aspect of the invention prolongs survival beyond that expected in the absence of treatment by 1 or months, preferably 3 or more months, more preferably 6 or more months, yet more preferably 1 or more years, preferably 2 or more, or 3 or more, even more preferably by 5 or more years, including 10 or more years. Providing a therapeutic effect also includes eliminating cancer cells. Providing a therapeutic effect also includes tumour mass reduction.

As used herein the term "irradiation" includes any suitable type and quantity of irradiation which provides a therapeutic effect. Suitable regimes of irradiation and examples of chemotherapeutic agents can be found in the current guidelines: 2011 Canada, Easaw et al., Current Oncology Vol 18 No 3.

As used herein the term "salt" includes base addition, acid addition and ammonium salts. 6-{4-[1-(Propan-2-yl)piperidin-4-yl]-1,4-diazepan-1-yl}-N-(pyridin-4-yl)pyridine-2-carboxamide is basic and so can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, trifluoroacetic, tartaric, succinic, fumaric, maleic, malic, salicylic, citric, methanesulphonic, p-toluenesulphonic, benzoic, benzenesulfonic, glutamic, lactic, and mandelic acids and the like. Those compounds which have a basic nitrogen can also form quaternary ammonium salts with a pharmaceutically acceptable counter-ion such as chloride, bromide, acetate, formate, p-toluenesulfonate, succinate, hemi-succinate, naphthalenebis sulfonate, methanesulfonate, trifluoroacetate, xinafoate, and the like. For a review on salts, see *Handbook of Pharmaceutical Salts: Properties, Selection, and Use* by Stahl and Wermuth (Wiley-VCH, Weinheim, Germany, 2002).

The compound "6-{4-[1-(Propan-2-yl)piperidin-4-yl]-1,4-diazepan-1-yl}-N-(pyridin-4-yl)pyridine-2-carboxamide" may exist as a solvate. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

The compound "6-{4-[1-(Propan-2-yl)piperidin-4-yl]-1,4-diazepan-1-yl}-N-(pyridin-4-yl)pyridine-2-carboxamide" may exist in an amorphous form and/or several polymorphic forms and may be obtained in different crystal habits. Any reference herein to 6-{4-[1-(Propan-2-yl)piperidin-4-yl]-1,4-diazepan-1-yl}-N-(pyridin-4-yl)pyridine-2-carboxamide includes all forms of that compound irrespective of amorphous or polymorphic form.

Pharmaceutical Preparations and Formulations

6-{4-[1-(Propan-2-yl)piperidin-4-yl]-1,4-diazepan-1-yl}-N-(pyridin-4-yl)pyridine-2-carboxamide for use in the present invention (i.e. either alone or in combination with irradiation and/or a chemotherapeutic agent) may be prepared in the form of a salt, especially a pharmaceutically acceptable salt, an N-oxide, a hydrate, a solvate and a polymorphic form thereof.

6-{4-[1-(Propan-2-yl)piperidin-4-yl]-1,4-diazepan-1-yl}-N-(pyridin-4-yl)pyridine-2-carboxamide may be administered in a variety of dosage forms. Thus, it can be administered orally, for example as a tablet, a capsule, a troche, a lozenge, an aqueous or oily suspension, a dispersible powder or granule. 6-{4-[1-(Propan-2-yl)piperidin-4-yl]-1,4-diazepan-1-yl}-N-(pyridin-4-yl)pyridine-2-carboxamide can be administered in a sublingual formulation, for example a buccal formulation. 6-{4-[1-(Propan-2-yl)piperidin-4-yl]-1,4-diazepan-1-yl}-N-(pyridin-4-yl)pyridine-2-carboxamide may also be administered parenterally, whether subcutaneously, intravenously, intramuscularly, intrasternally, transdermally, by inhalation, intranasally, or by infusion techniques. Thus, 6-{4-[1-(Propan-2-yl)piperidin-4-yl]-1,4-diazepan-1-yl}-N-(pyridin-4-yl)pyridine-2-carboxamide is administered orally, or by inhalation, or intranasally, but preferably the route of administration is oral or intravenous. In the event that 6-{4-[1-(Propan-2-yl)piperidin-4-yl]-1,4-diazepan-1-yl}-N-(pyridin-4-yl)pyridine-2-carboxamide is administered orally the preferred vehicle is a tablet or capsule. In the latter connection, administration of the compounds in a hard gelatine capsule form, or in one of the many sustained release formulations known in the art will often be preferred. In the event that the route of administration is intravenous, 6-{4-[1-(Propan-2-yl)piperidin-4-yl]-1,4-diazepan-1-yl}-N-(pyridin-4-yl)pyridine-2-carboxamide is administered as an aqueous solution.

6-{4-[1-(Propan-2-yl)piperidin-4-yl]-1,4-diazepan-1-yl}-N-(pyridin-4-yl)pyridine-2-carboxamide is typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar coating, or film coating processes.

Liquid dispersions for oral administration may be syrups, emulsions and suspensions. The syrups may contain as carriers, for example, saccharose or saccharose with glycerine and/or mannitol and/or sorbitol. Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the art. However, it is expected that a typical dose of 6-{4-[1-(Propan-2-yl)piperidin-4-yl]-1,4-diazepan-1-yl}-N-(pyridin-4-yl)pyridine-2-carboxamide will be in the range from about 0.001 to 50 mg per kg of body weight.

Synthesis

6-{4-[1-(Propan-2-yl)piperidin-4-yl]-1,4-diazepan-1-yl}-N-(pyridin-4-yl)pyridine-2-carboxamide may be prepared using techniques known to the skilled person, including, for example, the method set out in Scheme 1.

Scheme1. Synthetic Route for 6-{4-[1-(Propan-2-yl)piperidin-4-yl]-1,4-diazepan-1-yl}-N-(pyridin-4-yl)pyridine-2-carboxamide

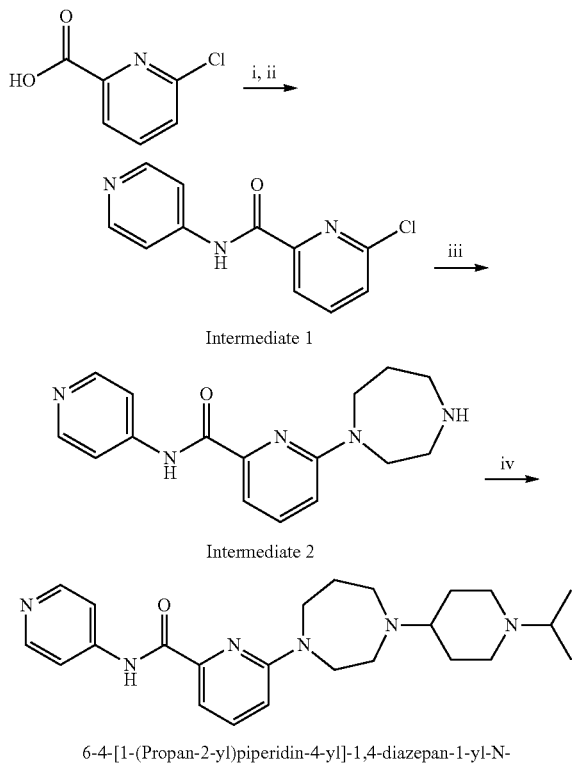

6-4-[1-(Propan-2-yl)piperidin-4-yl]-1,4-diazepan-1-yl-N-(pyridin-4-yl)pyridine-2-carboxamide i) (COCl)$_2$, DMF, DCM, ii) DIPEA, 4-Aminopyridine, DCM, iii) Homopiperazine, DMA, 180° C., microwave, iv) NaBH(OAc)$_3$, 1-(propan-2-yl)piperidin-4-one, DMC The following abbreviations have been used:
Aq aqueous
d day(s)
DCM Dichloromethane
DIPEA Diisopropylethylamine
DMA dimethylacetamide
DMF dimethylformamide
DMSO dimethyl sulfoxide
ES+ electrospray ionization
h hour(s)
HPLC High Performance Liquid Chromatography
IR Infrared Spectroscopy
LCMS Liquid Chromatography Mass Spectrometry
MeCN Acetonitrile
[MH]+ protonated molecular ion
min minute(s)
MS Mass Spectrometry
NMR Nuclear Magnetic Spectrometry
RP reverse phase
Rt retention time
sat saturated
TFA trifluoroacetic acid
UPLC Ultra Performance Liquid Chromatography

EXPERIMENTAL METHODS

All reagents were commercial grade and were used as received without further purification, unless otherwise specified. Reagent grade solvents were used, unless otherwise specified. The reactions facilitated by microwave heating were performed on a Biotage Initiator system. Preparative low pressure chromatography was performed using a CombiFlash Companion or Combiflash RF systems equipped with RediSep or GraceResolv silica and C18 reverse phase columns. Preparative reverse phase HPLC was performed on a Gilson system with a UV detector equipped with a ACE-5AQ, 100×21.20 mm, 5 mm or Phenomenex Synergi Hydro-RP 80A AXIA, 100×21.20 mm, 4 mm columns. The purest fractions were collected, concentrated and dried under vacuum. Compounds were typically dried in a vacuum oven between 40° C. and 60° C. prior to purity analysis. Analytical HPLC was performed on an Agilent 1100 system. Analytical LCMS was performed on an Agilent 1100 HPLC system with a Waters ZQ mass spectrometer. NMR was performed on a Bruker Avance 500 MHz Cryo Ultrashield with Dual CryoProbe. IR analysis was performed on a Perkin Elmer FT-IR Spectrum BX using a Pike MIRacle single reflection ATR. Melting point determination was performed on a Reichert Thermovar hotstage microscope. Reactions were performed at room temperature unless otherwise stated. The compounds were automatically named using IUPAC rules.

Intermediate 1

6-Chloro-N-(pyridin-4-yl)pyridine-2-carboxamide

6-Chloropyridine-2-carboxylic acid (5.50 g, 34.9 mmol) and DMF (0.5 mL) were dissolved in DCM (100 mL) and oxalyl chloride (7.09 mL, 83.8 mmol) was added. The reaction mixture was stirred for 0.5 h then the solvents were removed in vacuo. The residue was dissolved in DCM (100 mL) cooled to 0° C. DIPEA (14.6 mL, 83.8 mmol) and 4-aminopyridine (3.94 g, 41.9 mmol) were added and the reaction was allowed to warm to room temperature then stirred for a further 0.5 h. The solvents were removed in vacuo and the residue was partitioned between DCM (100 mL) and water (75 mL). The aqueous layer was extracted with DCM (2×75 mL), the organic layers combined, washed with $Na_2CO_3$ (1M, 75 mL), brine (75 mL), dried ($MgSO_4$) and the solvents removed in vacuo. The residue was purified by column chromatography to give the title compound (6.66 g, 81.7%) as an off white solid. LCMS (ES+): 234.2 [MH]+.

Intermediate 2

6-(1,4-Diazepan-1-yl)-N-(pyridin-4-yl)pyridine-2-carboxamide

Intermediate 1 (1.5 g, 6.42 mmol) was dissolved in DMA (12.5 mL). Homopiperazine (3.22 g, 32.1 mmol) was added and the reaction mixture was heated using a Biotage microwave at 180° C. for 0.5 h. This process was repeated three further times on the same scale and the four batches were combined and the solvent removed in vacuo. The residue was dissolved in DCM (300 mL) and washed with sat aq $Na_2CO_3$ solution (150 mL), brine (100 mL), dried ($MgSO_4$) and the solvents were removed in vacuo. The residue was purified by column chromatography to give the title compound (6.88 g, 90.1%) as light yellow solid. LCMS (ES+): 298.2 [MH]+.

6-{4-[1-(Propan-2-yl)piperidin-4-yl]-1,4-diazepan-1-yl}-N-(pyridin-4-yl)pyridine-2-carboxamide Intermediate 2 (4.88 g, 16.4 mmol) was dissolved in DCM (200 mL). 1-(Propan-2-yl)piperidin-4-one (4.88 mL, 32.8 mmol) and sodium triacetoxyborohydride (17.4 g, 82.1 mmol) were added and the reaction mixture stirred for 20 h. The reaction mixture was diluted with DCM (200 mL) and quenched with sat aq $Na_2CO_3$ solution (100 mL). The aqueous layer was extracted with DCM (100 mL). The organic layers were combined, washed with brine (50 mL), dried ($MgSO_4$) and the solvents removed in vacuo. The residue was purified by crystallisation from MeCN followed by reverse phase column chromatography. The residue was partitioned between DCM (300 mL) and sat aq $Na_2CO_3$ solution (100 mL). The aqueous layer was extracted with DCM (50 mL) and the organic layers were combined, washed with brine (50 mL), dried ($MgSO_4$) and the solvents removed in vacuo. The residue was crystallised from MeCN to give the title compound (4.66 g, 67.3%) as a light yellow solid.

HPLC: Rt 3.47 min, 100% purity
LCMS (ES+): 423.2 [MH]+
$^1$H NMR (500 MHz, DMSO-$d_6$) $\delta_H$ 10.31 (1H, s, NH), 8.52-8.50 (2H, m, ArH), 7.84-7.82 (2H, m, ArH), 7.70 (1H, dd, J 8.5 and 7.3 Hz, ArH), 7.30 (1H, d, J 7.2 Hz, ArH), 6.93 (1H, d, J 8.7 Hz, ArH), 3.80 (2H, m, NCH$_2$), 3.76 (2H, m, NCH$_2$), 2.82-2.79 (2H, m, NCH$_2$), 2.77-2.73 (2H, m, NCH$_2$), 2.62 (1H, spt, J 6.6 Hz, CHMe), 2.58-2.56 (2H, m, NCH$_2$), 2.39-2.33 (1H, m, NCHCH$_2$), 2.05-1.88 (2H, m, NCH$_2$), 1.85-1.78 (2H, m, CH$_2$), 1.65-1.60 (2H, m, NCHCH$_2$), 1.36 (2H, qd, J 11.7 and 3.4 Hz, NCHCH$_2$), 0.91 (6H, d, J 6.6 Hz, CH(CH$_3$)$_2$)
IR (solid) $v_{max}$/cm$^{-1}$ 3328, 2936, 2358, 2162, 1982, 1682, 1597, 1582, 1510, 1485, 1459, 1418, 1404, 1383, 1364, 1336, 1282, 1246, 1211, 1179, 1161, 1125, 1070, 1030, 994, 972, 926, 898, 878, 824, 814, 758, 681 and 617.
Melting point: 157-159° C.

The following examples are provided to further illustrate the embodiments of the present invention.

Example 1

In the experiment represented by FIG. 1, groups of 5 mice were injected with vehicle, AMD3100 (5 mg/kg) or injected sub cutaneously with 6-{4-[1-(Propan-2-yl)piperidin-4-yl]-1,4-diazepan-1-yl}-N-(pyridin-4-yl)pyridine-2-carboxamide (30 mg/kg) and the mobilisation of haematopoietic progenitor cells assessed 1 hour later. The data are expressed for the multipotential GEMM cells as colony forming units per ml of peripheral blood.

FIG. 1 reveals that 6-{4-[1-(Propan-2-yl)piperidin-4-yl]-1,4-diazepan-1-yl}-N-(pyridin-4-yl)pyridine-2-carboxamide does not result in significant mobilisation of HSCs from the mouse bone marrow. This is surprising in view of the known tendency of CXCR4 antagonists (such as AMD3100/Plerixafor/Mozobil) to mobilise HSCs. FIG. 1 shows that the mobilisation of HSCs by AMD3100 is significantly greater than that caused by vehicle (P<0.05). The reduced mobilisation of the HSCs from the protective environment of the bone marrow is expected to reduce the risk of side effects caused by destruction of HSCs by irradiation and/or a chemotherapeutic agent, such side effects including anaemia and neutropenia.

Example 2

Figure 2:
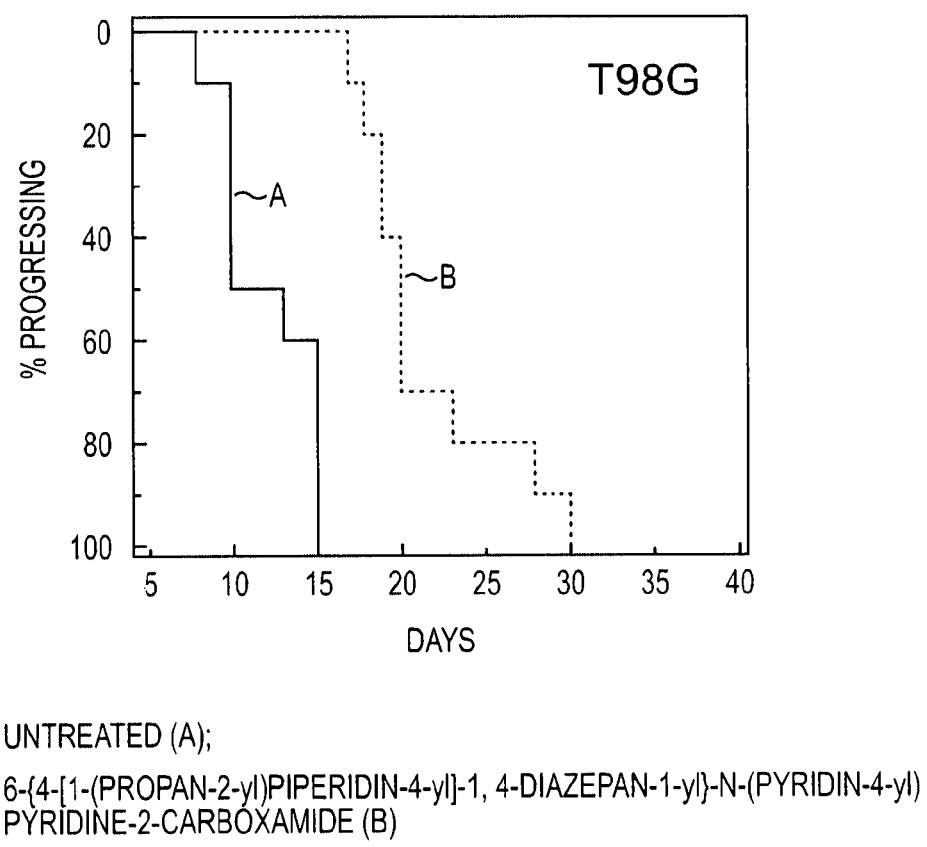
FIG. 2 is a graph showing that treatment with 6-{4-[1-(Propan-2-yl)piperidin-4-yl]-1,4-diazepan-1-yl}-N-(pyridin-4-yl)pyridine-2-carboxamide (dotted line) inhibits the growth of a human glioblastoma cell line (T98G) in nude mice subcutaneous xenografts compared to control (solid line).

In this Example, the efficacy of 6-{4-[1-(Propan-2-yl)piperidin-4-yl]-1,4-diazepan-1-yl}-N-(pyridin-4-yl)pyridine-2-carboxamide in inhibiting the growth of a human glioblastoma cell line (T98G) in nude mice subcutaneous xenografts was demonstrated (FIG. 2).

FIG. 2 shows the inhibition of T98G xenograft growth in nude mice by 6-{4-[1-(Propan-2-yl)piperidin-4-yl]-1,4-diazepan-1-yl}-N-(pyridin-4-yl)pyridine-2-carboxamide (50 mg/kg, once per day by oral gavage, for 5 days every week, dotted line). The solid line represents the control (i.e. untreated). The data in FIG. 2 are presented as % of the tumours progressing in groups of 8-10 mice, where progression is defined as a 20% increase in tumour volume. Tumour volume was determined by measuring the width and depth of the tumour with calipers, and then calculating the volume. The x axis shows the number of days. After 15 days all of the control mice had progressed, whereas none of the mice treated with 6-{4-[1-(Propan-2-yl)piperidin-4-yl]-1,4-diazepan-1-yl}-N-(pyridin-4-yl)pyridine-2-carboxamide had done so. Inhibition of growth of human glioblastoma cell line (T98G) in nude mice is expected to be predictive of a beneficial therapeutic outcome in human cancer patients, including patients suffering from glioblastoma and astrocytoma.

Example 3

Figure 3:
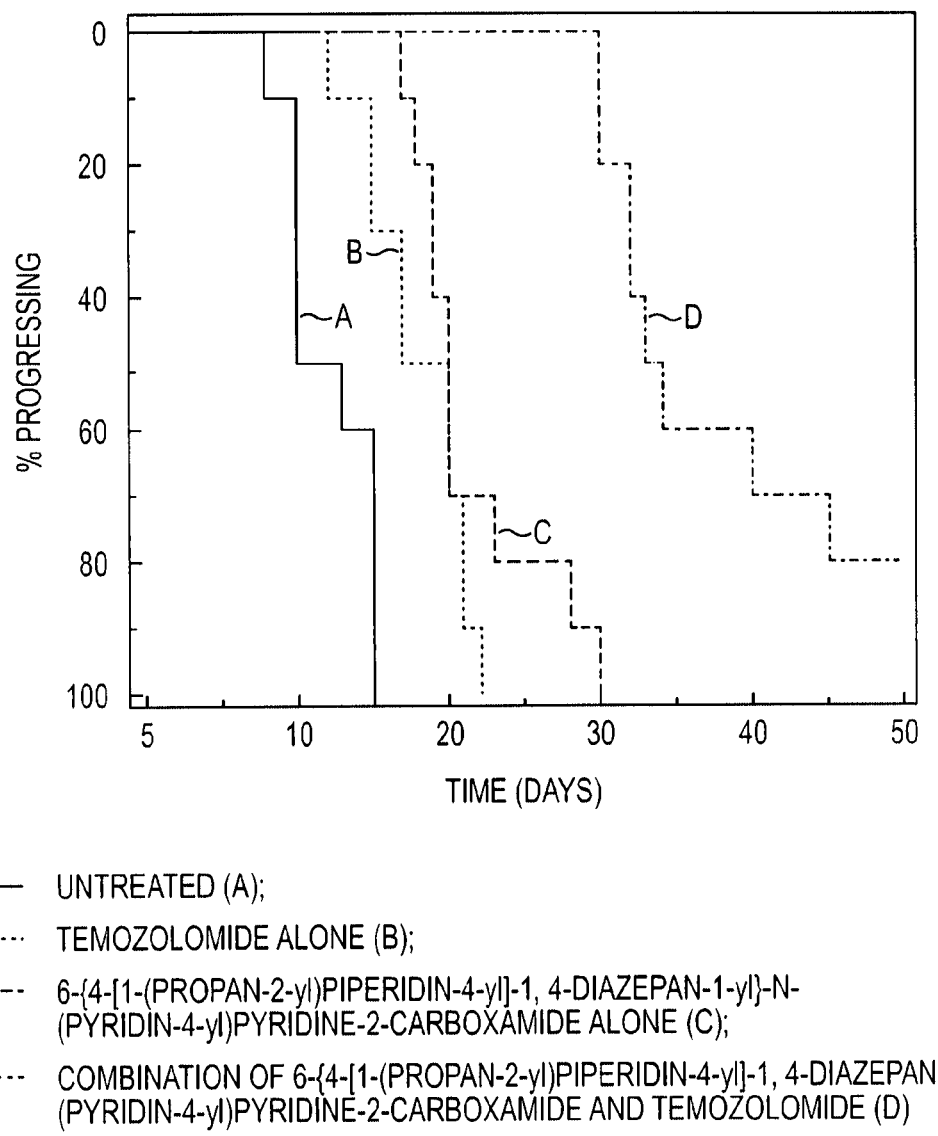
FIG. 3 is a graph showing that treatment with 6-{4-[1-(Propan-2-yl)piperidin-4-yl]-1,4-diazepan-1-yl}-N-(pyridin-4-yl)pyridine-2-carboxamide and the chemotherapeutic agent temozolomide inhibits the growth of a human glioblastoma cell line (T98G) in nude mice subcutaneous xenografts. Combining the two treatments resulted in surprisingly increased (i.e. synergistic) anti-tumour efficacy.

In this Example, the efficacy of 6-{4-[1-(Propan-2-yl)piperidin-4-yl]-1,4-diazepan-1-yl}-N-(pyridin-4-yl)pyridine-2-carboxamide in inhibiting the growth of a human glioblastoma cell line (T98G) in nude mice subcutaneous xenografts was demonstrated (FIG. 3). After the subcutaneous tumours had grown to at least 120 mm³ the mice were randomised into groups and treated with temozolomide (16 mg/kg po daily for 5 days) and 6-{4-[1-(Propan-2-yl)piperidin-4-yl]-1,4-diazepan-1-yl}-N-(pyridin-4-yl)pyridine-2-carboxamide (50 mg/kg, once per day by oral gavage, for 5 days every week, dotted line).

The data are presented in FIG. 3 as % of the tumours progressing in groups of 8-10 mice, where progression is defined as a 20% increase in tumour volume. The x axis shows the number of days; (——————) represents untreated mice; (- - - - - - - -) represents temozolomide alone; (••••••••) represents 6-{4-[1-(Propan-2-yl)piperidin-4-yl]-1,4-diazepan-1-yl}-N-(pyridin-4-yl)pyridine-2-carboxamide alone; and (—•—•—) represents the combination of 6-{4-[1-(Propan-2-yl)piperidin-4-yl]-1,4-diazepan-1-yl}-N-(pyridin-4-yl)pyridine-2-carboxamide and temozolomide.

FIG. 3 shows that treatment with 6-{4-[1-(Propan-2-yl)piperidin-4-yl]-1,4-diazepan-1-yl}-N-(pyridin-4-yl)pyridine-2-carboxamide and the brain penetrating chemotherapeutic agent temozolomide inhibits the growth of a human CNS cancer cell line (T98G) in nude mice subcutaneous xenografts. Combining the two treatments resulted in a surprisingly increased (i.e. synergistic) anti-tumour efficacy. The combination has an advantageously reduced risk of side effects due to the surprisingly low tendency of 6-{4-[1-(Propan-2-yl)piperidin-4-yl]-1,4-diazepan-1-yl}-N-(pyridin-4-yl)pyridine-2-carboxamide to liberate HSCs from the protective bone marrow environment.

Examples 4-10

Introduction

The efficacy of 6-{4-[1-(Propan-2-yl)piperidin-4-yl]-1,4-diazepan-1-yl}-N-(pyridin-4-yl)pyridine-2-carboxamide in inhibiting the growth of orthotopic (intracranial) tumours in nude mice alone, or in combination with bevacizumab, temozolomide, radiotherapy or Sunitinib, is demonstrated in FIGS. 4-7, 8A, 8B, 9A, 9B, and 10. In each graph the x axis shows the number of days. In the graphs in FIGS. 4-7 and 10, the y axis shows % survival (i.e. the % of mice not yet euthanised). In the graphs in FIGS. 8A, 8B, 9A, and 9B the y axis shows the % of the tumours progressing, where progression is defined as the point in time at which a tumour has grown to a size which is detectable by luminescence). The experiments represented by FIGS. 4, 5, and 6 had the same control (i.e. vehicle only), and therefore the same control data. For improved clarity, the line representing the control data has been removed from FIGS. 5 and 6, but retained in FIG. 4.

Materials and Methods

Unless indicated otherwise, the following materials and methods were used for Examples 4-10.

Nude mice were immobilized on a stereotaxic apparatus and anaesthetized. The operative field was prepared with betadine. A small hole was made at 1.0 mm anterior and 2 mm lateral to the exposed bregma. A sterile 5 µL Hamilton syringe with a 26 gauge needle was inserted at a depth of 3.0 mm from the skull surface and withdrawn by 0.5 mm to inject $3\times10^3$ U87MG cells in a volume of 3 µL. The injection rate was set up to 1 µL/min. After the implantation of the tumour cells, the needle was left in place for 5 min to prevent reflux. The needle was then completely withdrawn from the brain over the course of 4 min (1.0 mm/min), and the skin was sutured. Just before treatment initiation (5 days after injection), animals were randomized to treatment groups of 10 mice each. A small amount of cells was chosen ($3\times10^3$) to simulate a chemo-radiotherapic treatment made after surgery in which a low number of tumour cells remain in the operatory bed, re-grow and give arise to a recurrence. Treatments were started 5 days after cell injection when no luciferase activity was detectable intracranially, and continued for 35 days. Time to progression (i.e. detection of luminescence) was assessed, and the mice followed for up to 180 days. Mice were euthanized when they displayed neurological signs (e.g., altered gait, tremors/seizures, lethargy) or weight loss of 20% or greater of pre-surgical weight. The y axis parameter 'survival' is the percentage of mice not yet euthanised. The y axis parameter 'probability of detection' is the percentage of mice having a tumour that has progressed to the stage where luminescence is detected.

The following dosage administrations were used: 6-{4-[1-(Propan-2-yl)piperidin-4-yl]-1,4-diazepan-1-yl}-N-(pyridin-4-yl)pyridine-2-carboxamide was dosed at 50 mg/kg po once daily. Bevacizumab was dosed at 4 mg/kg iv every 4 days. Temozolomide was dosed at 32 mg/kg po daily. Sunitinib was dosed at 40 mg/kg po daily. Radiotherapy consisted of 3×2Gy daily.

RESULTS AND CONCLUSIONS

An increase in survival of nude mice having intracranial tumours formed from human glioblastoma cell lines such as U87MG is expected to be predictive of a beneficial therapeutic outcome in human cancer patients, including patients suffering from CNS cancers such as glioblastoma and astrocytoma.

An increase in the time taken for intracranial tumours formed from human glioblastoma cell lines such as U87MG to be detectable by luminescence in nude mice is expected to be predictive of a beneficial therapeutic outcome in human cancer patients, including patients suffering from CNS cancers such as glioblastoma and astrocytoma.

Figure 4:
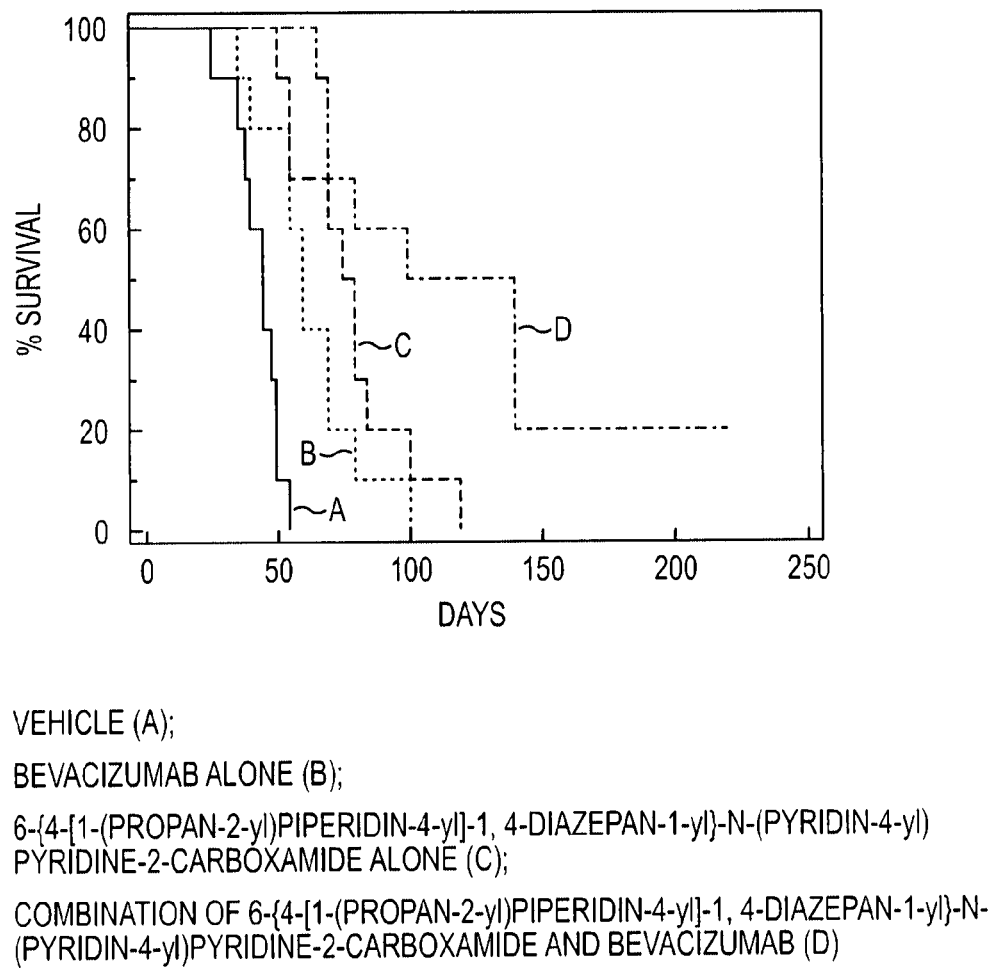
FIG. 4 is a graph showing that treatment with 6-{4-[1-(Propan-2-yl)piperidin-4-yl]-1,4-diazepan-1-yl}-N-(pyridin-4-yl)pyridine-2-carboxamide and the chemotherapeutic agent bevacizumab inhibits the growth of a tumour formed from a human glioblastoma cell line (U87MG) introduced intracranially into nude mice. Combining the two treatments results in surprisingly increased (i.e. synergistic) anti-tumour efficacy, as demonstrated by the increased duration of survival of mice with orthotopic (intracranial) tumours (combination p=0.002, HR 3.4 vs vehicle).

Turning now to the drawings, FIG. 4 shows that 6-{4-[1-(Propan-2-yl)piperidin-4-yl]-1,4-diazepan-1-yl}-N-(pyridin-4-yl)pyridine-2-carboxamide acts synergistically with Bevacizumab in increasing survival of mice with orthotopic (intracranial) tumours (combination p=0.002, HR 3.4 vs vehicle).

Figure 5:
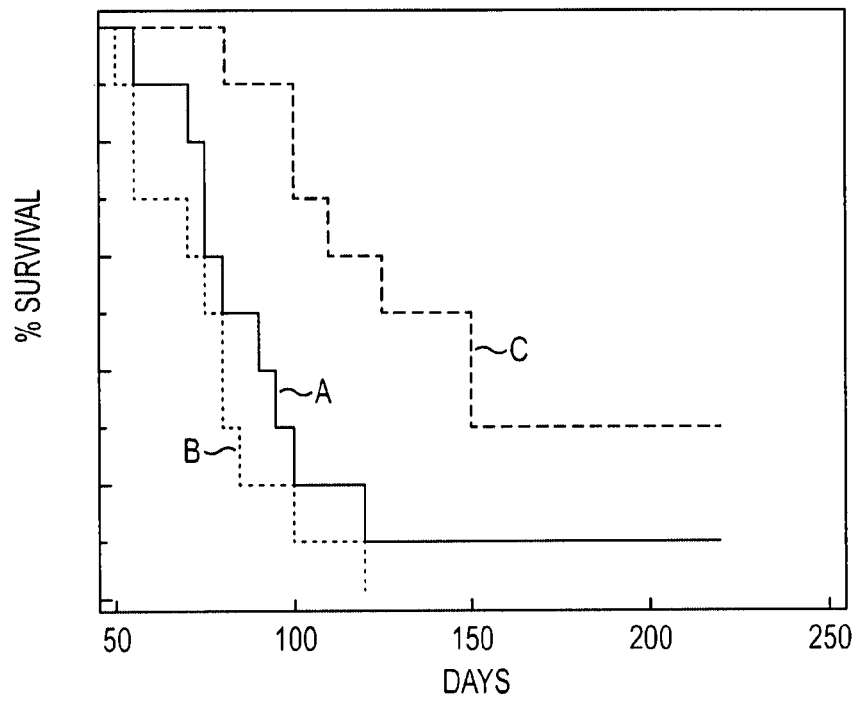
FIG. 5 is a graph showing that treatment with 6-{4-[1-(Propan-2-yl)piperidin-4-yl]-1,4-diazepan-1-yl}-N-(pyridin-4-yl)pyridine-2-carboxamide and the chemotherapeutic agent temozolomide inhibits the growth of a tumour formed from a human glioblastoma cell line (U87MG) introduced intracranially into nude mice. Combining the two treatments results in surprisingly increased (i.e. synergistic) anti-tumour efficacy, as demonstrated by the increased duration of survival of mice with orthotopic (intracranial) tumours (combination p=0.02, HR 2.8 vs temozolomide alone).

FIG. 5 shows that 6-{4-[1-(Propan-2-yl)piperidin-4-yl]-1,4-diazepan-1-yl}-N-(pyridin-4-yl)pyridine-2-carboxamide acts synergistically with Temozolomide in increasing survival of mice with orthotopic (intracranial) tumours (combination p=0.02, HR 2.8 vs Temozolomide alone).

Figure 6:
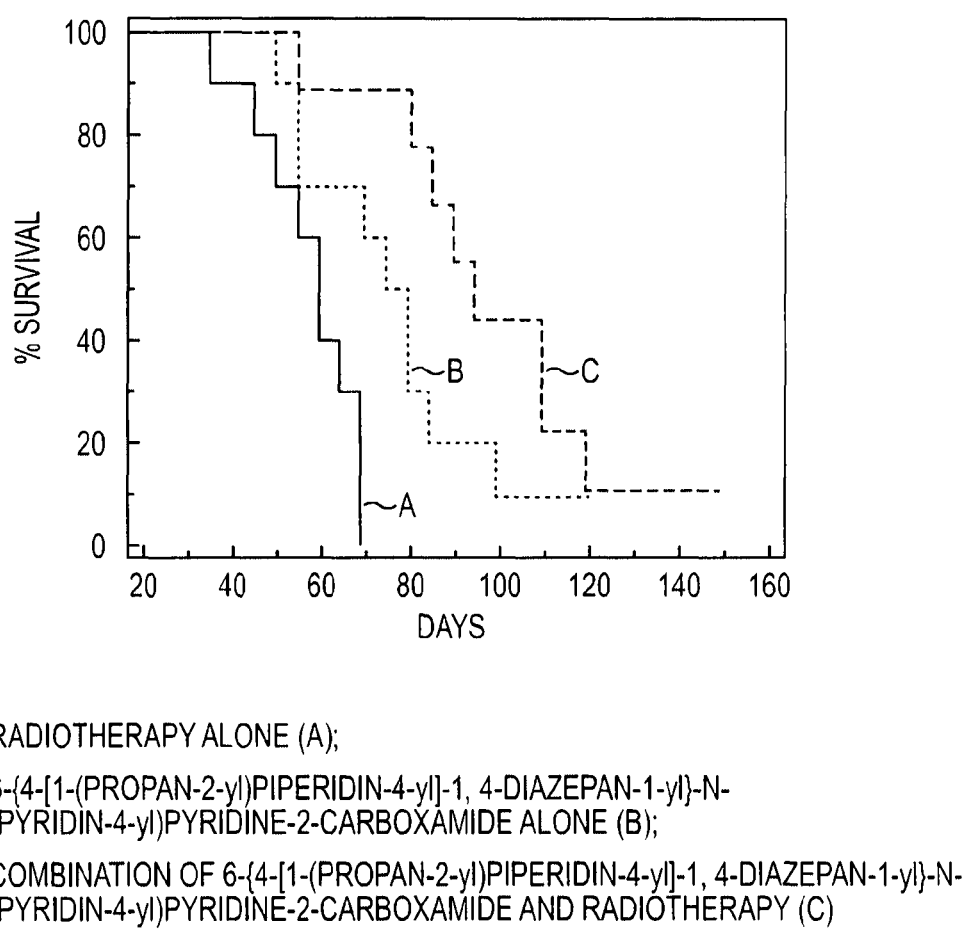
FIG. 6 is a graph showing that treatment with 6-{4-[1-(Propan-2-yl)piperidin-4-yl]-1,4-diazepan-1-yl}-N-(pyridin-4-yl)pyridine-2-carboxamide and radiotherapy inhibits the growth of a tumour formed from a human glioblastoma cell line (U87MG) introduced intracranially into nude mice. Combining the two treatments results in surprisingly increased (i.e. synergistic) anti-tumour efficacy, as demonstrated by the increased duration of survival of mice with orthotopic (intracranial) tumours (combination p=0.0002, HR 4.0 vs radiotherapy alone).

FIG. 6 shows that 6-{4-[1-(Propan-2-yl)piperidin-4-yl]-1,4-diazepan-1-yl}-N-(pyridin-4-yl)pyridine-2-carboxamide acts synergistically with radiotherapy in increasing survival of mice with orthotopic (intracranial) tumours (combination p=0.0002, HR 4.0 vs radiotherapy alone).

Figure 7:
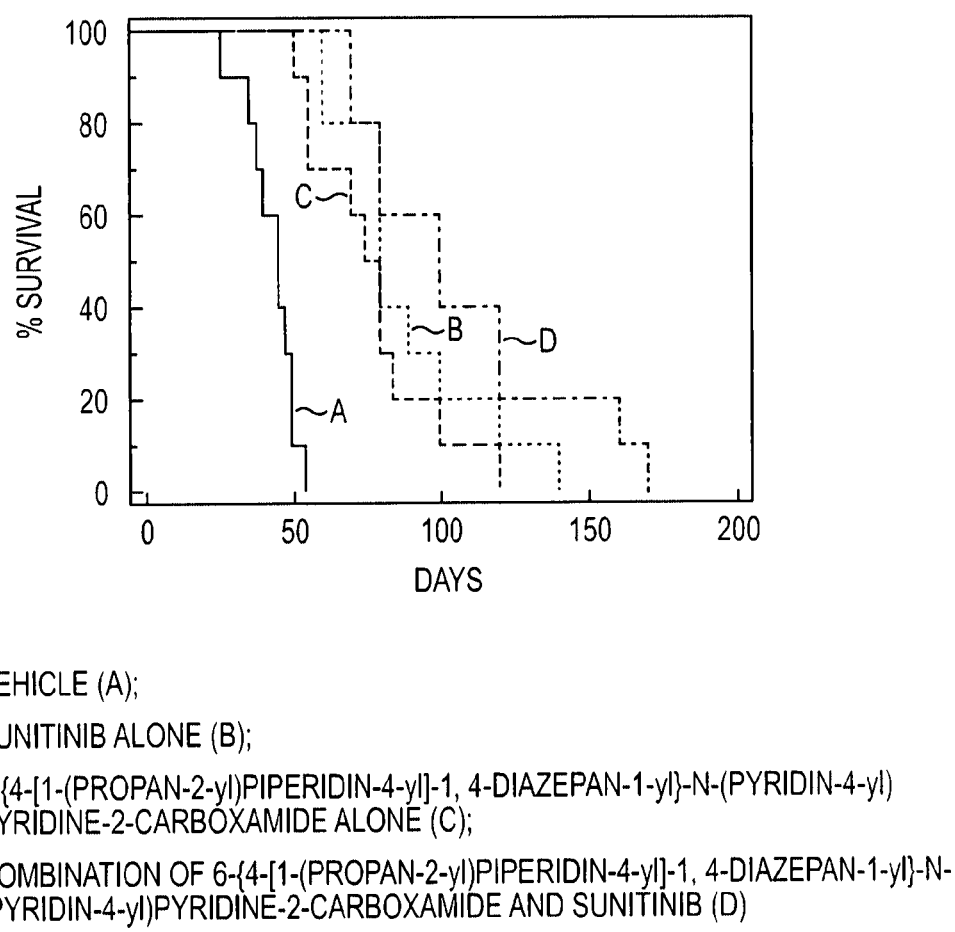
FIG. 7 is a graph showing that treatment with 6-{4-[1-(Propan-2-yl)piperidin-4-yl]-1,4-diazepan-1-yl}-N-(pyridin-4-yl)pyridine-2-carboxamide and sunitinib inhibits the growth of a tumour formed from a human glioblastoma cell line (U87MG) introduced intracranially into nude mice. Combining the two treatments results in surprisingly increased (i.e. synergistic) anti-tumour efficacy, as demonstrated by the increased duration of survival of mice with orthotopic (intracranial) tumours (combination p=0.2, HR 1.6 vs vehicle).

FIG. 7 shows that 6-{4-[1-(Propan-2-yl)piperidin-4-yl]-1,4-diazepan-1-yl}-N-(pyridin-4-yl)pyridine-2-carboxamide enhanced synergistically the effects of Sunitinib in increasing survival of mice with orthotopic (intracranial) tumours (combination p=0.2, HR 1.6 vs vehicle).

Figure 8A:
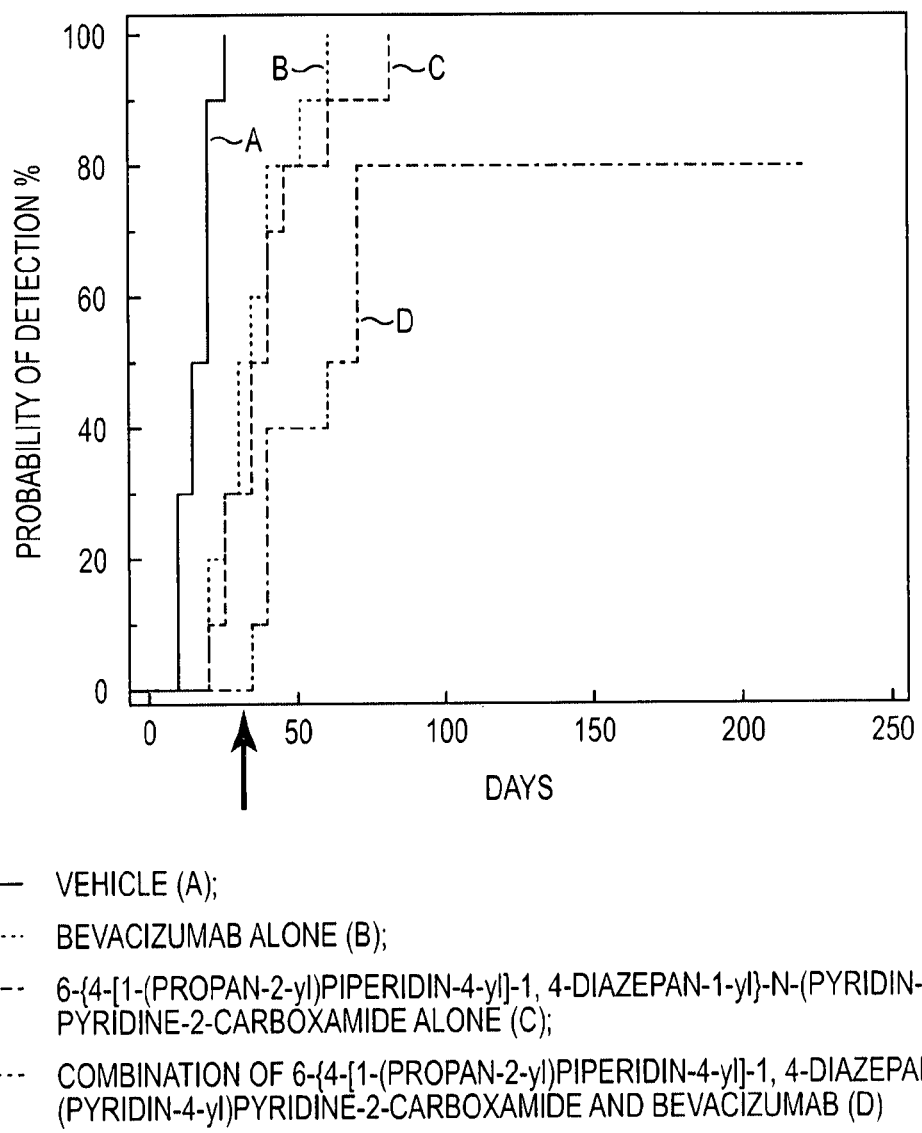
FIGS. 8A and 8B are graphs showing that treatment with 6-{4-[1-(Propan-2-yl)piperidin-4-yl]-1,4-diazepan-1-yl}-N-(pyridin-4-yl)pyridine-2-carboxamide delays the growth of a tumour formed from a human glioblastoma cell line (U87MG) introduced intracranially into nude mice, and that 6-{4-[1-(Propan-2-yl)piperidin-4-yl]-1,4-diazepan-1-yl}-N-(pyridin-4-yl)pyridine-2-carboxamide acts synergistically with bevacizumab or sunitinib in delaying or inhibiting the growth of tumours. The arrow on the X axis indicated end of dosing.
Figure 8B:
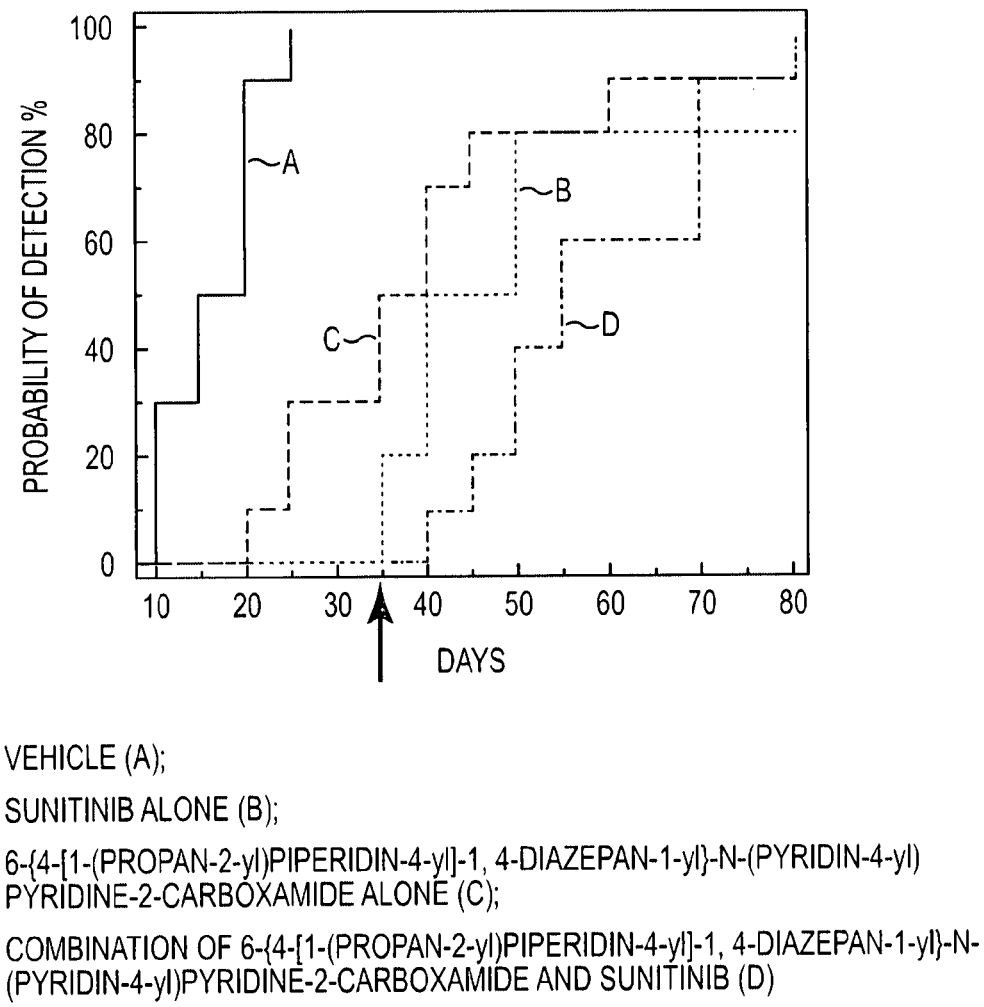

As shown in FIGS. 8A and 8B, 6-{4-[1-(Propan-2-yl)piperidin-4-yl]-1,4-diazepan-1-yl}-N-(pyridin-4-yl)pyridine-2-carboxamide acts synergistically with Bevacizumab or Sunitinib in increasing the time taken for progression of tumours, thus demonstrating inhibition of tumour growth and increased probability of survival (FIG. 8A; combination p=0.0001, HR 9.7 vs vehicle) and Sunitinib (Figure B; combination p=0.0001, HR 5.3 vs vehicle). 6-{4-[1-(Propan-2-yl)piperidin-4-yl]-1,4-diazepan-1-yl}-N-(pyridin-4-yl)pyridine-2-carboxamide delayed the growth of the tumour to a size detectable through luminescence (H.R. 3.5 to vehicle). The combination of 6-{4-[1-(Propan-2-yl)piperidin-4-yl]-1,4-diazepan-1-yl}-N-(pyridin-4-yl)pyridine-2-carboxamide with Bevacizumab or Sunitinib shows significantly increased growth delay compared to 6-{4-[1-(Propan-2-yl)piperidin-4-yl]-1,4-diazepan-1-yl}-N-(pyridin-4-yl) pyridine-2-carboxamide, Bevacizumab and Sunitinib alone. The Y axis in FIGS. 8A and 8B are the same, namely: probability of detection (%).

Figure 9A:
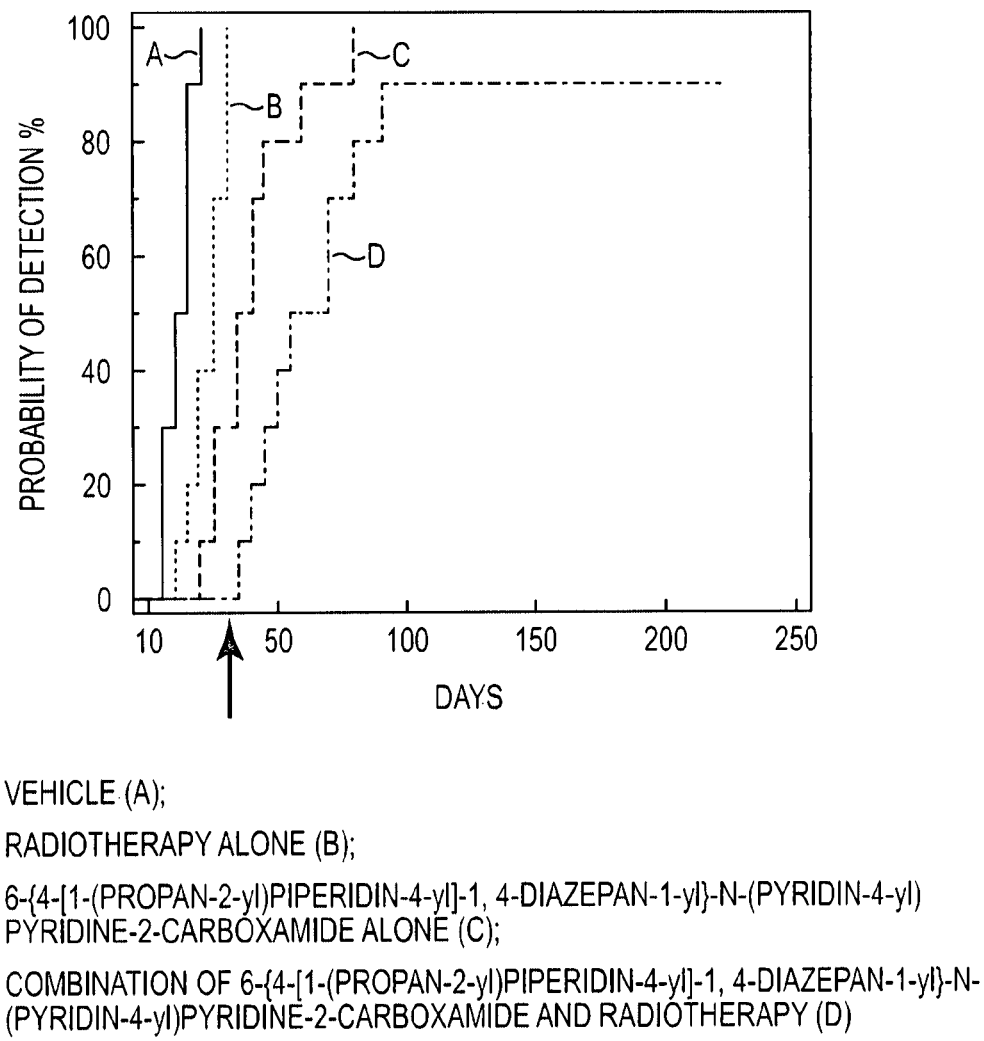
FIGS. 9A and 9B are graphs showing that treatment with 6-{4-[1-(Propan-2-yl)piperidin-4-yl]-1,4-diazepan-1-yl}-N-(pyridin-4-yl)pyridine-2-carboxamide delays intracranial tumour growth and acts synergistically with irradiation treatment (FIG. 9A) and temozolomide treatment (FIG. 9B) in delaying or inhibiting the growth of a tumour formed from a human glioblastoma cell line (U87MG) introduced intracranially into nude mice. The arrow on the X axis indicates end of dosing.
Figure 9B:
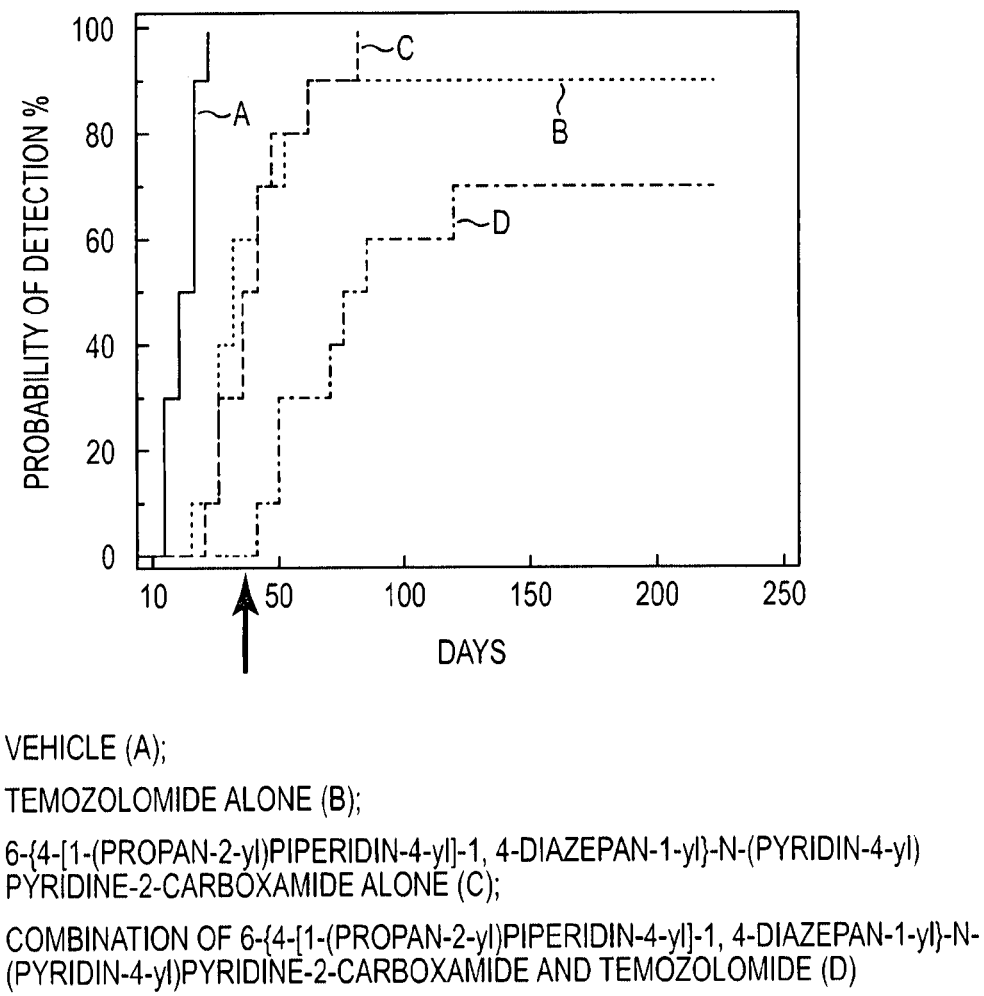

As shown in FIGS. 9A and 9B, 6-{4-[1-(Propan-2-yl) piperidin-4-yl]-1,4-diazepan-1-yl}-N-(pyridin-4-yl)pyridine-2-carboxamide acts synergistically with irradiation and/or temozolomide in the treatment of intracranial tumours. Dosing with 6-{4-[1-(Propan-2-yl)piperidin-4-yl]-1,4-diazepan-1-yl}-N-(pyridin-4-yl)pyridine-2-carboxamide alone delayed tumour growth, (HR 3.7, p<0.001), and surprisingly increases the efficacy of irradiation treatment (FIG. 9A; irradiation p=0.0001, HR 4.6 vs combination) and temozolomide treatment (FIG. 9B; temozolomide p=0.01, HR 2.9 vs combination). The Y axis in FIGS. 9A and 9B are the same, namely: probability of detection (%).

Figure 10:
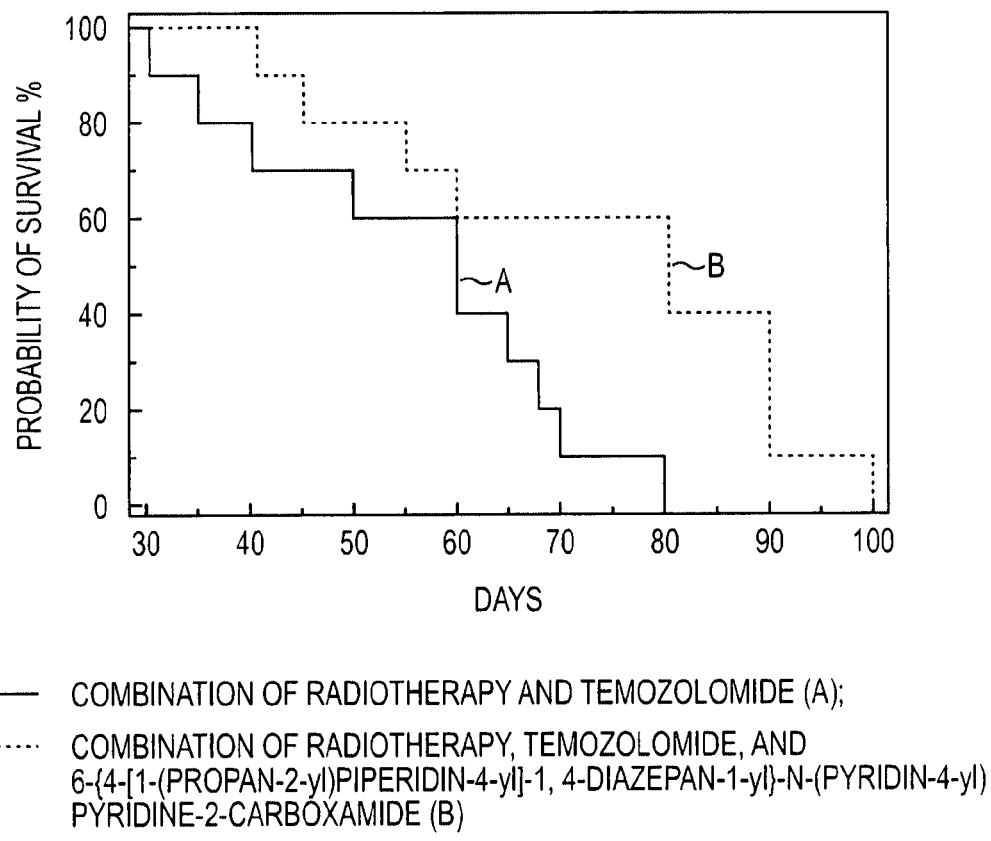
FIG. 10 is a graph showing that treatment with 6-{4-[1-(Propan-2-yl)piperidin-4-yl]-1,4-diazepan-1-yl}-N-(pyridin-4-yl)pyridine-2-carboxamide surprisingly increases the effectiveness of combined temozolomide and irradiation treatment in the survival of mice with orthotopic (intracranial) tumours. The arrow on the X axis indicates end of dosing.

As shown in FIG. 10, treatment with 6-{4-[1-(Propan-2-yl)piperidin-4-yl]-1,4-diazepan-1-yl}-N-(pyridin-4-yl)pyridine-2-carboxamide acts synergistically with irradiation treatment and temozolomide treatment on the survival of mice with orthotopic (intracranial) tumours (combination p=0.025, HR 2.3). For this experiment, 5×10$^3$ U87MG cells were injected using the technique described above. Following injection of the U87MG cells, tumours were detectable in the mice, which were treated for 28 days.

The invention claimed is:

1. A method of mitigating blood-related side effects from radiation therapy in a glioblastoma patient in need thereof, which method comprises administering to the patient a therapeutically effective amount of 6-{4-[1-(propan-2-yl) piperidin-4-yl]-1,4-diazepan-1-yl}-N-(pyridin-4-yl)pyridine-2-carboxamide, or a pharmaceutically acceptable salt thereof, wherein the patient subsequently receives radiation therapy after the administering step.

2. The method of claim 1, wherein the patient subsequently receives radiation therapy within 24 hours of the administering step.

3. The method of claim 1, wherein the method further comprises administering irradiation to the patient.

4. The method of claim 1, wherein 6-{4-[1-(Propan-2-yl) piperidin-4-yl]-1,4-diazepan-1-yl}-N-(pyridin-4-yl)pyridine-2-carboxamide is in an intravenous formulation.

5. The method of claim 1, wherein 6-{4-[1-(Propan-2-yl) piperidin-4-yl]-1,4-diazepan-1-yl}-N-(pyridin-4-yl)pyridine-2-carboxamide is administered in an amount of from about 0.001 to about 50 mg per kg of body weight.

6. The method of claim 1, further comprising administering a chemotherapeutic agent.

7. The method of claim 6, wherein the chemotherapeutic agent is temozolomide.

* * * * *